United States Patent
Melnyk et al.

(10) Patent No.: US 11,166,926 B2
(45) Date of Patent: Nov. 9, 2021

(54) COMPOSITIONS AND METHODS FOR PROTECTING A HOST FROM ENTERIC TOXIGENIC PATHOGENS

(71) Applicants: The Hospital For Sick Children, Toronto (CA); University of Maryland, Baltimore, Baltimore, MD (US)

(72) Inventors: Roman Alexander Melnyk, Oakville (CA); Hanping Feng, Ellicott City, MD (US); Therwa Hamza, Laurel, MD (US)

(73) Assignees: THE HOSPITAL FOR SICK CHILDREN, Toronto (CA); UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 16/535,658

(22) Filed: Aug. 8, 2019

(65) Prior Publication Data

US 2020/0046659 A1 Feb. 13, 2020

Related U.S. Application Data

(60) Provisional application No. 62/715,975, filed on Aug. 8, 2018.

(51) Int. Cl.
| | | |
|---|---|---|
| *A61K 31/167* | (2006.01) | |
| *A61P 31/04* | (2006.01) | |
| *A61K 45/06* | (2006.01) | |

(52) U.S. Cl.
CPC ............ *A61K 31/167* (2013.01); *A61P 31/04* (2018.01); *A61K 45/06* (2013.01)

(58) Field of Classification Search
CPC .............................. A61K 31/167; A61P 31/04
See application file for complete search history.

(56) References Cited

FOREIGN PATENT DOCUMENTS

| | | | | |
|---|---|---|---|---|
| WO | WO-2016193136 A1 * | 12/2016 | ........... | A61K 31/612 |
| WO | WO-2018013890 A1 * | 1/2018 | ........... | A61K 31/277 |

OTHER PUBLICATIONS

Gooyit et al., "Reprofiled anthelmintics abate hypervirulent stationary-phase Clostridium difficile," Sci. Rep. (Nature) 2016;6:33642. PMID: 27633064. (Year: 2016).*
Niclosamide Ethanolamine Commercial Availability, retrieved from STN/CHEMCATS on Oct. 28, 2020. (Year: 2015).*

* cited by examiner

*Primary Examiner* — Theodore R. Howell
(74) *Attorney, Agent, or Firm* — Myers Bigel, P.A.

(57) ABSTRACT

A method of protecting a host from an enteric toxigenic pathogen comprises administering a salicylanilide to the host. A method of reducing virulence of an enteric toxigenic pathogen comprises administering a salicylanilide to a host infected with or at risk of infection with pathogen. A method of reducing recurrence of an infection caused by an enteric toxigenic pathogen, comprises administering a salicylanilide to a host previously infected with the pathogen.

19 Claims, 11 Drawing Sheets

| Drug | % inhibition of cell rounding |
|---|---|
| QUINACRINE HYDROCHLORIDE | 98, 82, 80 |
| Carvedilol | 92 |
| EBSELEN | 82 |
| AMODIAQUINE DIHYDROCHLORIDE | 77 |
| Nocodazole | 74 |
| Rotenone | 73 |
| CHLORTETRACYCLINE HYDROCHLORIDE | 72 |
| BENZETHONIUM CHLORIDE | 72 |
| Niclosamide | 71 |
| 5-(N,N-hexamethylene)amiloride | 70 |
| MUNDULONE | 69 |
| MECLOCYCLINE SULFOSALICYLATE | 68 |
| CHICAGO SKY BLUE | 67 |
| CISPLATIN | 66 |
| Bay 11-7085 | 65 |
| ZM 39923 hydrochloride | 65 |
| CETYLPYRIDINIUM CHLORIDE | 63 |
| Hexahydro-sila-difenidol hydrochloride, p-fluoro analog | 62 |
| Bay 11-7082 | 62 |
| CHLOROQUINE DIPHOSPHATE CRYSTALLINE | 61 |
| 3-(1H-Imidazol-4-yl)propyl di(p-fluorophenyl)methyl ether hydrochloride | 61 |
| HEXACHLOROPHENE | 60 |
| CLOSANTEL | 60 |
| Pifithrin-mu | 59 |
| HYDROQUINONE | 58 |
| Vincristine sulfate | 57 |
| Loratadine | 57 |
| Sanguinarine chloride | 56 |
| MONENSIN SODIUM | 56 |
| Perphenazine | 55 |
| PHENYL AMINOSALICYLATE | 55 |
| 2,3-DIHYDROXY-4-METHOXY-4'-ETHOXYBENZOPHENONE | 55 |
| 3-METHOXYCATECHOL | 55 |
| Chelerythrine chloride | 54 |
| AURIN TRICARBOXYLIC ACID | 54 |
| CGP-74514A hydrochloride | 54 |
| Emetine dihydrochloride hydrate | 53 |
| Cisplatin | 53 |
| DICHLOROPHEN | 53 |
| ONONETIN | 52 |
| TETRAMIZOLE HYDROCHLORIDE | 52 |
| Z-L-Phe chloromethyl ketone | 51 |
| AMINACRINE | 51 |
| Piceatannol | 51 |
| Picropodophyllotoxin | 51 |
| OXIBENDAZOLE | 50 |
| CEARDIN | 50 |
| GR 127935 hydrochloride hydrate | 50 |
| U-73122 | 50 |
| AGARIC ACID | 50 |
| CARMUSTINE | 50 |
| Vinblastine sulfate salt | 49 |
| DEOXYSAPPANONE B 7,3'-DIMETHYL ETHER ACETATE | 48 |
| EPIGALLOCATECHIN-3-MONOGALLATE | 48 |
| Colchicine | 46 |
| Supercinnamaldehyde | 46 |
| CCG-4986 | 45 |
| 4-Phenyl-3-furoxancarbonitrile | 45 |
| SKF 96365 | 45 |
| OXYCLOZANIDE | 43 |

Fig. 5

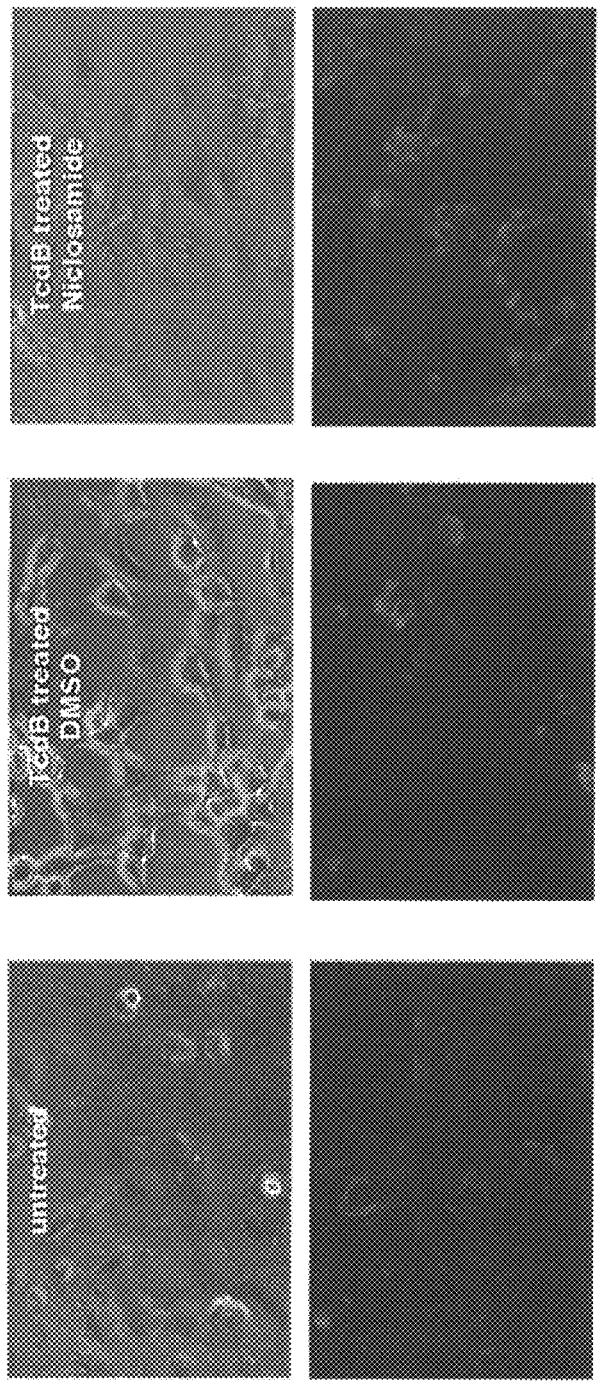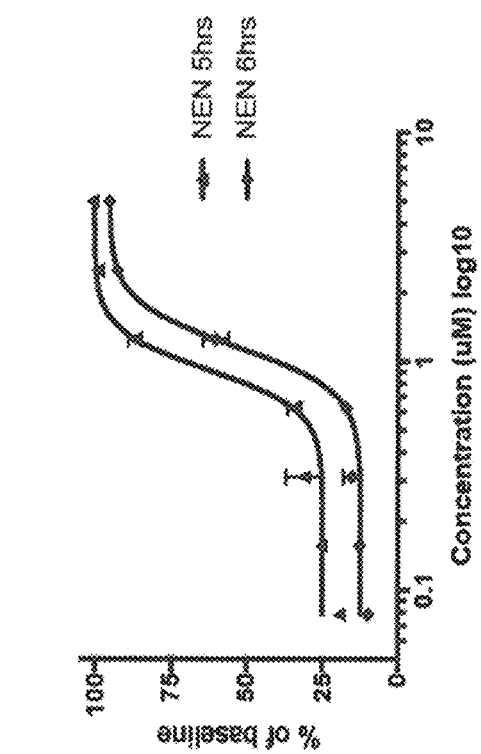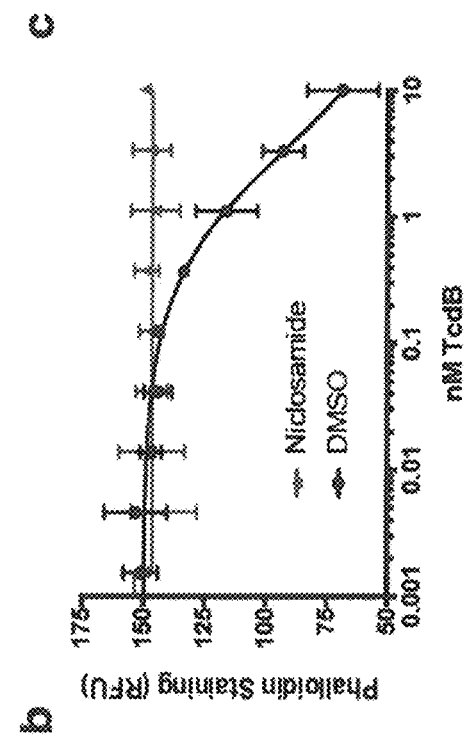
Fig. 6

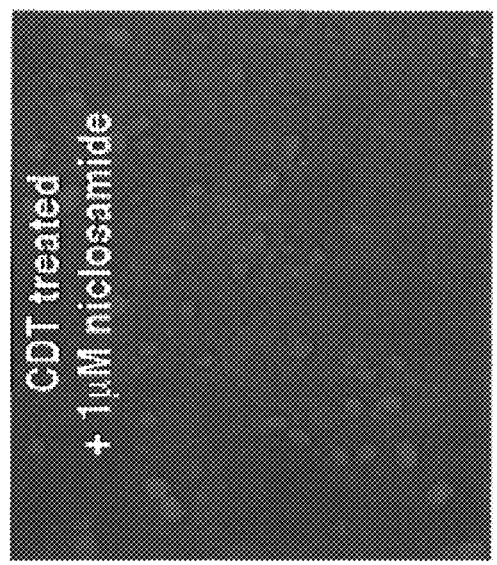
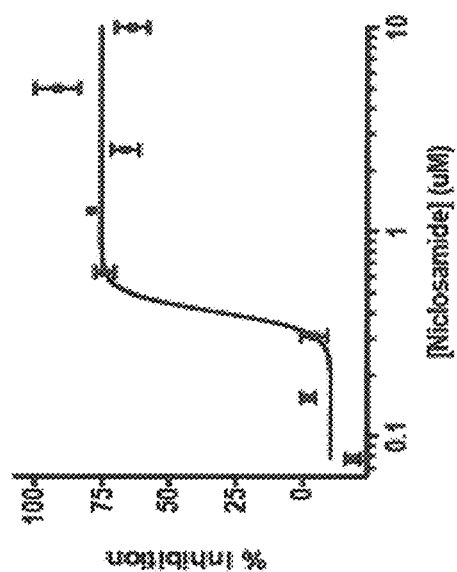
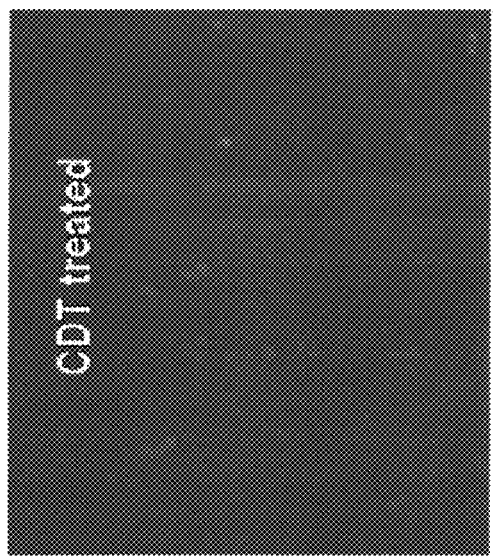
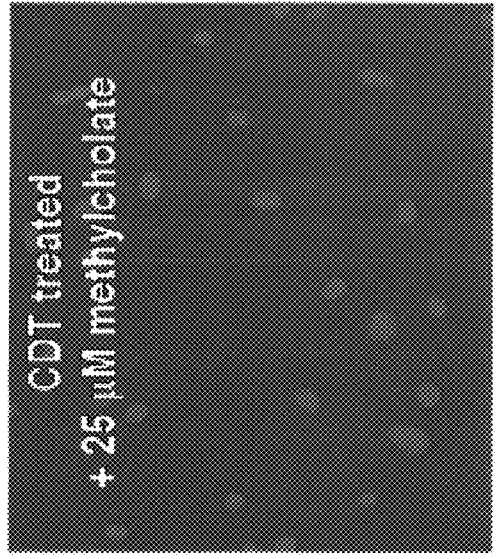
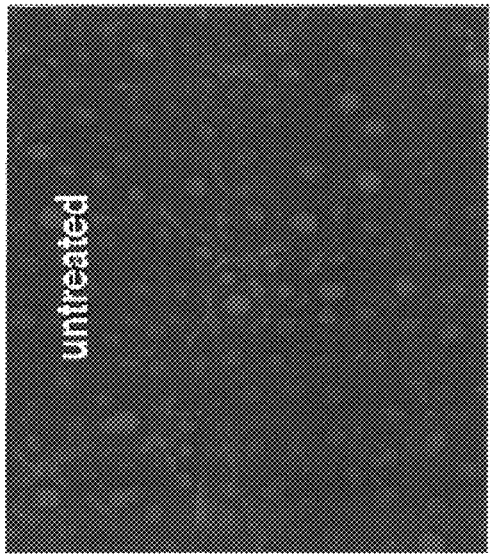
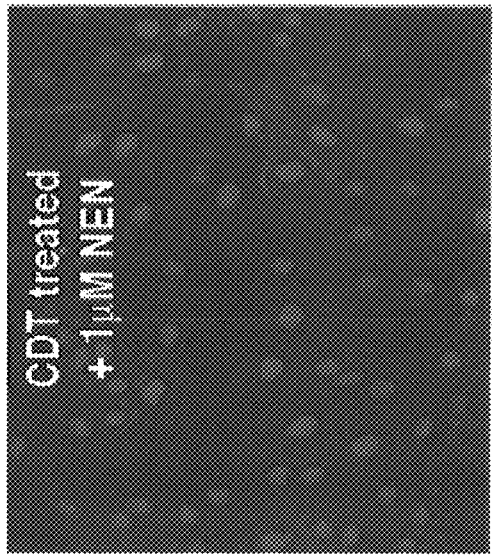
Fig. 8

COMPOSITIONS AND METHODS FOR PROTECTING A HOST FROM ENTERIC TOXIGENIC PATHOGENS

STATEMENT OF PRIORITY

This application claims the benefit, under 35 U.S.C. § 119 (e), of U.S. Provisional Application Ser. No. 62/715,975 filed on Aug. 8, 2018, the entire contents of which is incorporated by reference herein.

FIELD

The present invention relates to *Clostridium* infections. More specifically, the present invention is, in aspects, concerned with compositions and methods for reducing *Clostridium* virulence.

BACKGROUND

*Clostridium difficile* infection (CDI or C-dif) is a symptomatic infection due to the spore-forming bacterium, *Clostridium difficile*. Symptoms include watery diarrhea, fever, nausea, and abdominal pain. It makes up about 20% of cases of antibiotic-associated diarrhea. Complications may include pseudomembranous colitis, toxic megacolon, perforation of the colon, and sepsis.

Risk factors for infection include antibiotic or proton pump inhibitors use, hospitalization, other health problems, and older age. If a person tests positive but has no symptoms, the condition is known as *C. difficile* colonization rather than an infection. When the cause is antibiotic use, discontinuation of antibiotics may result in resolution of symptoms within three days in about 20% of those infected. Often the antibiotics metronidazole, vancomycin, or fidaxomicin will cure the infection but there are resistant strains. Recurrences have been reported in up to 25% of people.

Salicylanilides are a chemical class of anthelmintic active ingredients with efficacy against certain roundworms, tapeworms and/or flukes. All salicylanilides have a narrow spectrum of activity, and each one is effective only against certain parasites. They are used mainly in cattle and sheep.

International Patent Application Publication No. WO 2016/193136 relates to halogenated salicylanilides, or pharmaceutically acceptable salts or esters thereof, for use in the treatment of an infection in a subject caused by *Clostridium* bacteria, particularly a *C. difficile* infection. By broth microdilution techniques, it was determined that the salicylanilides were bactericidal against several different *C. difficile* strains in vitro.

Gooyit and Janda (Scientific reports 6, 33642 (2016)) describe the broad inhibition of *C. difficile* growth in vitro via a membrane depolarization mechanism by salicylanilides. By broth microdilution techniques, it was determined that the salicylanilides were bactericidal against logarithmic- and stationary-phase cultures of the CI/NAP1/027 strain 4118.

There is a need for alternative compositions to overcome or mitigate at least some of the deficiencies of the prior art, or to provide a useful alternative.

SUMMARY

In accordance with an aspect, there is provided a method of protecting a host from an enteric toxigenic pathogen, the method comprising administering a salicylanilide to the host.

In accordance with an aspect, there is provided a method of reducing virulence of an enteric toxigenic pathogen, the method comprising administering a salicylanilide to a host infected with or at risk of infection with the pathogen.

In accordance with an aspect, there is provided a method of reducing recurrence of an infection caused by an enteric toxigenic pathogen, the method comprising administering a salicylanilide to a host previously infected with the pathogen.

In an aspect, the host does not currently have an active or clinically relevant infection caused by the pathogen.

In an aspect, the pathogen is bacteria.

In an aspect, the bacteria is *Clostridium, Vibrio cholerae*, or *E. coli*.

In an aspect, the *Clostridium* is *C. difficile*.

In an aspect, the *C. difficile* is selected from ribotype 017, 027, 033, and 078.

In an aspect, the *Clostridium* expresses TcdA, and/or TcdB, and/or CDT.

In an aspect, the method reduces virulent toxin entry into host cells.

In an aspect, the salicylanilide is selected from the group consisting of bromochlorosalicylanilide, tetrachlorosalicylanilide, closantel, rafoxanide, oxyclozanide, resorantel, clioxanide, dibromosalan, tribromosalan, brotianide, niclosamide, salts thereof, esters thereof, derivatives thereof, and analogs thereof.

In an aspect, the salicylanilide is niclosamide ethanolamine (NEN).

In an aspect, the salicylanilide is not niclosamide.

In an aspect, the salicylanilide is used in an amount that affects host cells without substantially killing the pathogen and/or disrupting the gut microbiota.

In an aspect, the salicylanilide maintains gut microbiota diversity, composition, and/or structure.

In an aspect, the method does not cause antibiotic-induced dysbiosis of the GI microbiota.

In an aspect, the method at least partially restores the gut microbiota during the resolution phase of infection.

In an aspect, the method at least partially inhibits host damage induced by toxins without substantially altering the gut microbiota.

In an aspect, the salicylanilide acts on host cells through inhibition of the pore-formation process.

In an aspect, the salicylanilide increases the pH of host cell endosomal compartments.

In an aspect, the salicylanilide inhibits the pathogenesis of enterogenic toxins by targeting a host process required for entry into colonocytes by each toxin.

In an aspect, the toxins are selected from TcdA, and/or TcdB, and/or CDT.

In an aspect, the toxins are TcdA, TcdB, and CDT.

In an aspect, the salicylanilide protects the host from pathogen-related weight loss, death, and/or diarrhea.

In an aspect, the method reduces primary infection and/or recurrence of infection.

In an aspect, the salicylanilide is used as a stand-alone therapy.

In an aspect, the method is used as a first line therapy.

In an aspect, the method is used as a second line therapy once conventional antibiotics fail.

In an aspect, the method is for reducing recurrence and is for use after a conventional treatment.

In an aspect, the salicylanilide is used in combination with an antibiotic.

In an aspect, the host is a human, livestock such as cattle or sheep, poultry such as a chicken, or a pet such as a dog.

In accordance with an aspect, there is provided a method of treating and/or preventing a *Clostridium* infection or recurrence of a *Clostridium* infection, the method comprising administering NEN to a subject infected with or at risk of infection with *Clostridium*.

In accordance with an aspect, there is provided a method of reducing antibiotic-induced diarrhea in a subject, the method comprising treating the subject with a salicylanilide before, during, and/or after antibiotic treatment.

In an aspect, the diarrhea is caused by an enteric toxigenic pathogen.

In an aspect, the pathogen is *Clostridium*.

In an aspect, the antibiotic is for treating a non-*Clostridium* infection.

In accordance with an aspect, there is provided a method of preventing or reducing the risk of transmission or spread of *C. difficile* infection, for example spread of infection in a community or hospital environment, the method comprising administering a salicylanilide to a subject in the community or hospital environment.

In accordance with an aspect, there is provided a method of raising endosomal pH, the method comprising administering a salicylanilide.

In accordance with an aspect, there is provided a method of treating a condition associated with low endosomal pH, the method comprising administering a salicylanilide.

In an aspect, the condition is in the gut.

In accordance with an aspect, there is provided an oral toxin-neutralizing composition for treatment of an enteric toxigenic pathogen, the composition comprising a salicylanilide.

In an aspect, the pathogen is *Clostridium*.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from said detailed description.

DESCRIPTION OF THE FIGURES

The present invention will be further understood from the following description with reference to the Figures, in which:

FIG. 5. Table of hits from high throughput screen for inhibitors of TcdB-induced cell rounding. Molecules that inhibited TcdB-induced cell rounding by greater than three standard deviations of the mean of the total data are shown.

FIG. 6. Niclosamide protects Caco-2 cells from TcdB. (a) bright field and fluorescence images of Caco-2 cells. (b) TcdB-induced reduction in Phalloidin staining is prevented by niclosamide treatment. (c) TEER assay. NEN dose-dependently protects Caco-2 cell monolayers.

FIG. 8. CDT-induced toxicity of Vero cells in the presence of niclosamide, NEN and methlycholate (control). Cells were stained with 1 uM Hoechst for 30 min, then combined photos were taken for each compound at a concentration corresponding to maximum protection from TcdB using a 10× objective and appropriate filter sets for Hoechst and Alexa488 fluorescence (Zeiss).

DETAILED DESCRIPTION

Figure 1:
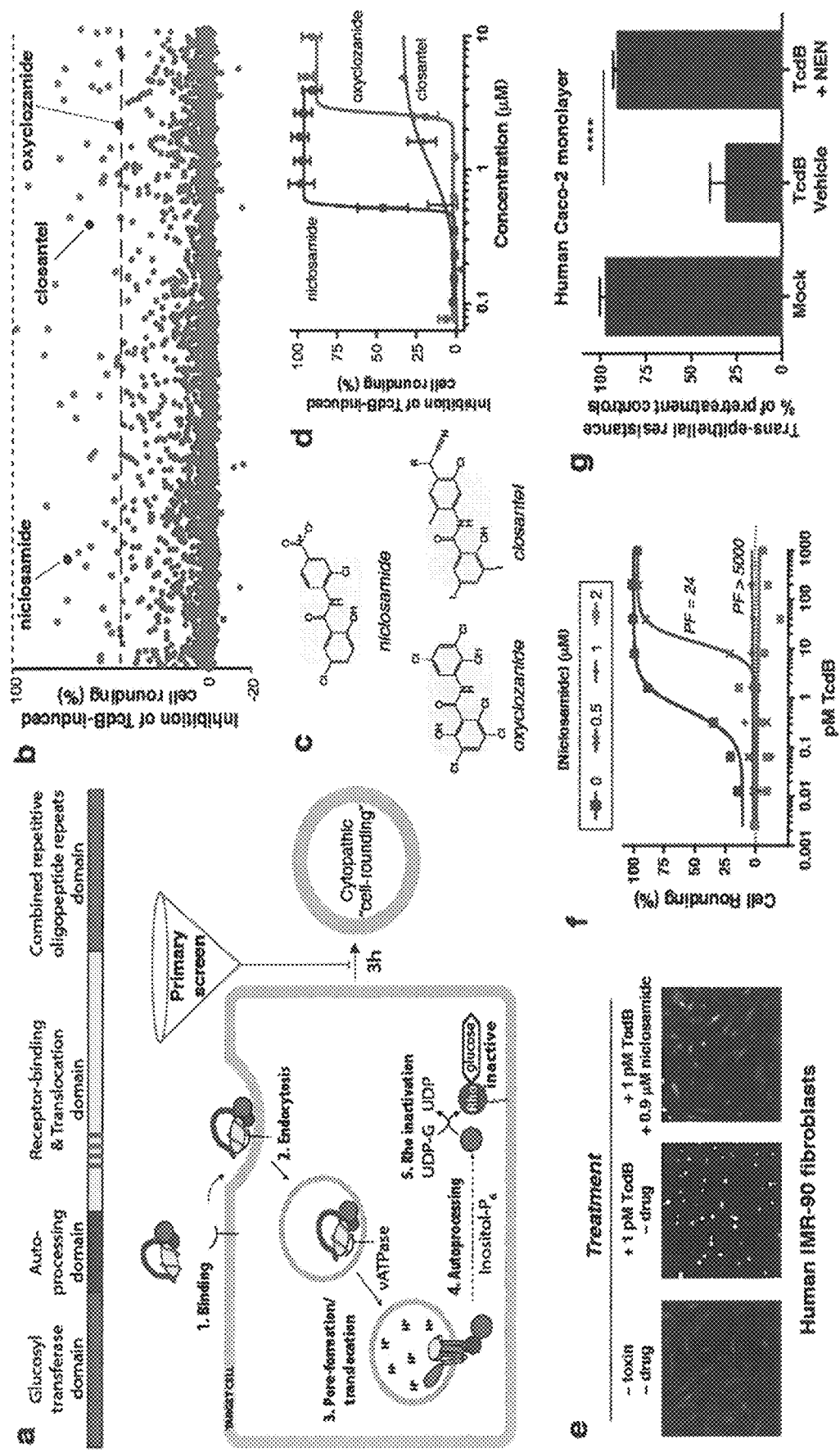
FIG. 1. Identification of niclosamide and other salicylanilide anthelmintic drugs from an imaging-based high-throughput screen of TcdB-induced cell-rounding. (a) Top, domain architecture of TcdB, highlighting the four domains involved in TcdB-induced cell-rounding. Membrane-insertion elements that are thought to form the translocation pore within endosomes (33) are depicted as orange vertical lines within the receptor-binding & translocation domain. Bottom, steps involved in TcdB intoxication of human cells. Chemical libraries were screened at 40 µM using an algorithm developed previously (30). (b) Results from high-throughput screening of 3580 drugs from the LOPAC and Microsource collections. A statistical cutoff of 43% inhibition of cell rounding was based on identification of molecules that were greater than 3-standard deviations above the mean of the data. The salicylanilide anthelmintic drugs niclosamide, closantel and oxyclozanide were among the 60 hits identified. (c) Chemical structures of niclosamide, oxyclozanide and closantel. (d) Dose titration curves of the inhibition of cell-rounding by niclosamide, oxyclozanide and closantel (n=5). Values represent mean±s.e.m. (e) Representative images of human IMR-90 fibroblasts. Cells were pre-treated with DMSO or niclosamide 15 minutes before treatment with buffer or TcdB and images were collected 3 h later. (f) Intoxication of human IMR-90 cells by TcdB in the presence of different doses of niclosamide. Protection factor, PF, represents the extent to which niclosamide shifts the curve for TcdB (i.e., $EC50_{niclosamide}/EC50_{vehicle}$). (g) Normalized trans-epithelial resistance measurements in human CaCo-2 cells, 6 h post treatment. 5 µM NEN significantly increased resistance across Caco-2 monolayer cells to mock control values (n=3). Values represent mean±s.e.m. ****p<0.0001.

Described herein are novel compositions and methods for treating toxin-mediated enteric infections, such as *Clostridium difficile*. We now demonstrate, using the gold standard method for determining *Clostridium* MIC, that salicylanilides are effective in treating and/or preventing *C. difficile* infection through their actions on host cells rather than actions on the bacteria cells. By increasing endosomal pH, salicylanilides prevent bacterial toxins from being taken up into host cells and thereby reduce or inhibit their virulence.

A common problem associated with *C. difficile* infection is the recurrence of the infection following initial antibiotic treatment. Often a patient will respond well to the initial antibiotic treatment and will be symptom free for a period of time. However, in many patients recurrence of the infection is common and is often more severe than the initial infection. Mortality rates increase as the frequency of recurrent infection increases. The compositions and methods described herein are suitable for reducing the recurrence of such an infection.

Definitions

For purposes herein, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987.

As used herein, "treatment" or "therapy" is an approach for obtaining beneficial or desired clinical results. For the purposes described herein, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" and "therapy" can also mean prolonging survival as compared to expected survival if not receiving treatment or therapy. Thus, "treatment" or "therapy" is an intervention performed with the intention of altering the pathology of a disorder. Specifically, the treatment or therapy may directly prevent, slow down or otherwise decrease the pathology of a disease or disorder such as an infection, or may render the cells more susceptible to treatment or therapy by other therapeutic agents.

Accordingly in the context of treating infections caused by a *Clostridium* bacteria, "treatment" includes one or more of at least:

(i) the prevention of a disease caused by *Clostridium* species, particularly *Clostridium difficile*;

(ii) the suppression of a disease caused by *Clostridium* species, particularly *Clostridium difficile*;

(iii) the relief of symptoms of a disease caused by *Clostridium* species, particularly *Clostridium difficile*;

(iv) the eradication of a non-symptomatic colonization by *Clostridium* species, particularly *Clostridium difficile* from an area on or in the body;

(v) the eradication of a *Clostridium difficile* symptomatic infection;

(vi) the eradication a *Clostridium* species, particularly *Clostridium difficile*; from an area of the body affected by another disease that could enable establishment of an infection more readily, than in a non-disease affected area—e.g. in the intestinal tract;

(vii) the suppression of a disease caused a *Clostridium* infection, particularly *Clostridium difficile*; from an area of the body affected by another non-infectious disease that enables establishment of an infection more readily, than in a non-disease affected area;

(viii) preventing or reducing the risk of transmission or spread of a *Clostridium* infection, particularly *Clostridium difficile*; and/or (ix) preventing or reducing the risk of recurrence of a *Clostridium* infection, particularly *Clostridium difficile*.

A "therapeutically effective amount" means the amount of a compound that, when administered to a subject, for example a human, for treating a disease, is sufficient to effect such treatment for the disease. The "therapeutically effective amount" will vary depending on the compound, the disease and its severity and the age, weight, etc., of the subject to be treated.

The terms "therapeutically effective amount", "effective amount" or "sufficient amount" mean a quantity sufficient, when administered to a subject, including a mammal, for example a human, to achieve a desired result, for example an amount effective to treat and/or prevent an infection. Effective amounts of the compounds described herein may vary according to factors such as the disease state, age, sex, and weight of the subject. Dosage or treatment regimes may be adjusted to provide the optimum therapeutic response, as is understood by a skilled person.

Moreover, a treatment regime of a subject with a therapeutically effective amount may consist of a single administration, or alternatively comprise a series of applications. The length of the treatment period depends on a variety of factors, such as the severity of the disease, the age of the subject, the concentration of the agent, the responsiveness of the patient to the agent, or a combination thereof. It will also be appreciated that the effective dosage of the agent used for the treatment may increase or decrease over the course of a particular treatment regime. Changes in dosage may result and become apparent by standard diagnostic assays known in the art. The compounds described herein may, in aspects, be administered before, during or after treatment with conventional therapies for the disease or disorder in question, such as an infection.

The term "host" or "subject" as used herein refers to any member of the animal kingdom, typically a mammal or bird, such as poultry. The term "mammal" refers to any animal classified as a mammal, including humans, other higher primates, domestic and farm animals, and zoo, sports, or pet animals, such as dogs, cats, cattle, horses, sheep, pigs, goats, rabbits, etc. Typically, the mammal is human. The subject may be a human aged 65 years or older. The treatment of animals infected with *C. difficile* with may be particularly effective for preventing spread of infection through animal faecal matter to humans or other animals.

Administration "in combination with" one or more further therapeutic agents includes simultaneous (concurrent) and consecutive administration in any order.

The term "pharmaceutically acceptable" means that the compound or combination of compounds is compatible with the remaining ingredients of a formulation for pharmaceutical use, and that it is generally safe for administering to humans according to established governmental standards, including those promulgated by the United States Food and Drug Administration.

The term "pharmaceutically acceptable carrier" includes, but is not limited to solvents, dispersion media, coatings, antibacterial agents, antifungal agents, isotonic and/or absorption delaying agents and the like. The use of pharmaceutically acceptable carriers is well known.

Included herein are pharmaceutically acceptable salts, esters, solvates and prodrugs of the compounds described herein and mixtures thereof.

In understanding the scope of the present application, the articles "a", "an", "the", and "said" are intended to mean that there are one or more of the elements. Additionally, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

It will be understood that any aspects described as "comprising" certain components may also "consist of" or "consist essentially of," (or vice versa) wherein "consisting of" has a closed-ended or restrictive meaning and "consisting essentially of" means including the components specified but excluding other components except for materials present as impurities, unavoidable materials present as a result of processes used to provide the components, and components added for a purpose other than achieving the technical effect of the invention. For example, a composition defined using the phrase "consisting essentially of" encompasses any known pharmaceutically acceptable additive, excipient, diluent, carrier, and the like. Typically, a composition consisting essentially of a set of components will comprise less than 5% by weight, typically less than 3% by weight, more typically less than 1% by weight of non-specified components.

It will be understood that any component defined herein as being included may be explicitly excluded from the claimed invention by way of proviso or negative limitation, such as any specific salicylanilides or bacteria species or strains whether implicitly or explicitly defined herein.

In addition, all ranges given herein include the end of the ranges and also any intermediate range points, whether explicitly stated or not.

Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Salicylanilides

A wide range of salicylanilides and derivatives are known. Any salicylanilide possessing antibacterial activity against *Clostridium* may be used in the methods described herein. For example, the salicylanilide may be any of the niclosamide analogues described in WO 2008/021088, which are incorporated herein by reference. The salicylanilide may also be any of the halogenated salicylanilides described in WO 2016/193136, which are incorporated herein by reference. For example, salicylanilide may be selected from the group consisting of bromochlorosalicylanilide, tetrachlorosalicylanilide, closantel, rafoxanide, oxyclozanide, resorantel, clioxanide, dibromosalan, tribromosalan, brotianide, niclosamide, NEN, 4'-chloro-3-nitrosalicylanilide, 4'-chloro-5-nitrosalicylanilide, 2'-chloro-5'-methoxy-3-nitro-sallcylanilide, 2'-methoxy-3,4'-dinitrosalicylanilide, 2',4'-dimethyl-3-nitrosalicylanilide, 2'-chloro-3,4'-dinitrosalicylanilide, 2'-ethyl-3-nitrosalicylanilide and 2'-bromo-3-nitrosalicyl-anilide or a pharmaceutically acceptable salt or ester thereof. Typically, the salicylanilide is a halogenated salicylanilide, such as niclosamide or niclosamide ethanolamine (NEN).

Compositions

The salicylanilides described herein, in aspects, are formulated into compositions. For example, provided herein is an oral toxin-neutralizing composition for treatment of an enteric toxigenic pathogen. The composition comprises a salicylanilide, typically in combination with a pharmaceutically acceptable carrier and, optionally, another agent such as an antibiotic.

The compositions described herein can be prepared by per se known methods for the preparation of pharmaceutically acceptable compositions that can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, 20th ed., Mack Publishing Company, Easton, Pa., USA, 2000). On this basis, the compositions may include, albeit not exclusively, the salicylanilides in association with one or more pharmaceutically acceptable vehicles or diluents, and may be contained in buffered solutions with a suitable pH that are iso-osmotic with physiological fluids.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of the subject. Other components that may be present in such compositions include water, surfactants (such as Tween), alcohols, polyols, glycerin and vegetable oils, for example. Extemporaneous injection solutions and suspensions may be prepared from sterile powders, granules, tablets, or concentrated solutions or suspensions. The pharmaceutical composition may be supplied, for example, but not by way of limitation, as a lyophilized powder which is reconstituted with sterile water or saline prior to administration to the patient.

Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1 (2,3-dioleyloxy)propyl)N,N,N-trimethylammonium chloride (DOTMA), diolesylphosphotidyl-ethanolamine (DOPE), and liposomes. Such compositions should contain a therapeutically effective amount of the active agent, together with a suitable amount of carrier so as to provide the form for direct administration to the patient.

Methods of Use

The salicylanilides described herein find use in treating any disorder in which increasing endosomal pH would be useful. Examples include treating enteric toxigenic infections, wherein the salicylanilides reduce the ability of host cells to uptake the toxins produced by pathogens. To this regard, it is contemplated that the salicylanilides described herein may be used in combination with conventional treatments for infection, such as antibiotics or fecal transplant, resulting in an additive or synergistic treatment modality. In aspects, the enteric pathogen is, for example, *Campylobacter jejuni, Salmonella, Salmonella typhimurium, Salmonella enterica* serovar *Typhi, Shigella* dystenteriae, *Plesiomonas shigelloides, Escherichia coli* including, but not limited to, (EPEC) enteropathogenic *E. coli*, (ETEC) enterotoxigenic *E. coli*, (EaggEC) enteroaggregative *E. coli*, (EIEC) enteroinvasive *E. coli*, and (EHEC) haemorrhagic *E. coli*], *Yersinia enterocolitica, Vibrio cholerae* O1, *Vibrio* O139, Non-O1 Vibrios, *Vibrio parahaemolyticus, Aeromonas hydrophile, Clostridium perfringens, Clostridium difficile,* enterohepatic *Helicobacter* (including, but not limited to, *Helicobacter pylori*), *Staphylococcus aureus, Klebsiella,* rotavirus, coronavirus, norovirus, calicivirus, enteric adenovirus, cytomegalovirus, and astrovirus. The toxin includes an endotoxin or exotoxin.

Thus, in aspects, provided herein is a method of protecting a host from an enteric toxigenic pathogen. In other aspects, provided herein is a method of reducing virulence of an enteric toxigenic pathogen. In other aspects, provided herein is a method of reducing recurrence of an infection caused by an enteric toxigenic pathogen. The pathogen may be any pathogen, including those listed above. The method comprises administering a salicylanilide to the host, such as bromochlorosalicylanilide, tetrachlorosalicylanilide, closantel, rafoxanide, oxyclozanide, resorantel, clioxanide, dibromosalan, tribromosalan, brotianide, niclosamide, salts thereof, esters thereof, derivatives thereof, or analogs thereof, or any other salicylanilide that acts in substantially the same way to increase endosome pH. The host may be experiencing a first or recurrent infection.

It will be understood that the salicylanilide acts on the host cells to reduce or prevent uptake of toxins and thereby reduces the virulence of the infection. Surprisingly, little if any effect is observed on the pathogen itself as well as the beneficial microbes in the gut. Thus, the treatment affects host cells without substantially killing the pathogen and/or disrupting the gut microbiota. In aspects, the salicylanilide maintains gut microbiota diversity, composition, and/or structure and/or does not cause antibiotic-induced dysbiosis of the GI microbiota. In certain aspects, the methods described herein at least partially restores the gut microbiota during the resolution phase of infection and/or at least partially inhibits host damage induced by toxins without substantially altering the gut microbiota. Typically, the salicylanilide acts on host cells through inhibition of the pore-formation process and/or increases the pH of host cell endosomal compartments, thereby inhibiting the pathogenesis of enterogenic toxins by targeting a host process required for entry into colonocytes by each toxin.

As the treatment maintains the natural microbiota and also maintains or improves the health of the subject or mitigates pathogenic effects on the health of the subject, the balance of microbes in the gut can be restored over time, either through additional interventions such as fecal transplant, probiotic treatment, or antibiotic treatment, or through natural competition amongst the microbes in the gut.

The host that is being treated in the methods described herein may or may not currently have an active or clinically relevant infection caused by the pathogen. Many pathogenic bacteria are carried by hosts without causing a problematic infection. The methods described herein may be used preventatively, in order to reduce the risk of infection or recurrent infection, or they may be used to treat an active or subclinical infection.

The observed effect does not appear to be toxin-specific. Thus, the toxin that is responsible for the virulence of the pathogen and is treated or prevented by the methods and compositions described herein can be any known toxin that acts on host cells after being taken up in endosomes. For example, with *Clostridium*, the toxin may be TcdA, and/or TcdB, and/or CDT. Typically, the method reduces virulent toxin entry into host cells.

Thus, the methods described herein in aspects protect the host from pathogen-related weight loss, death, and/or diarrhea and/or reduce primary infection and/or recurrence of infection. The salicylanilide may be used as a stand-alone therapy, as a first line therapy, or as a second line therapy once conventional antibiotics fail. The salicylanilide may be used for reducing recurrence after a conventional treatment and may be used in combination with an antibiotic.

It will be understood that the methods described herein may have use in reducing antibiotic-induced diarrhea in a subject. For example, subjects undergoing antibiotic treatment for something unrelated to an enteric pathogen, such as a wound, may have antibiotic-mediated disruption of the gut microbiota, allowing a subclinical *Clostridium* infection to become problematic. In aspects, this can be mitigated by treating the subject with a salicylanilide before, during, and/or after antibiotic treatment.

In other aspects, the methods described herein may find use in preventing or reducing the risk of transmission or spread of *C. difficile* infection, for example spread of infection in a community or hospital environment. By administering a salicylanilide to a subject, or several subjects, or most subjects, in the community or hospital environment, transmission can be reduced or prevented.

More generally, the methods described herein can be used for raising endosomal pH by administering a salicylanilide. This may be useful as a research tool in vitro or may find use in any disease or condition in which raising endosomal pH may be useful. For example, the pH levels in endosomes play an important role in many functions of endocytosis, including release of iron from transferrin, release of LDL and other ligands from their receptors, and activation of lysosomal hydrolases. Thus, the methods described herein may find use in diseases such as Alzheimer's disease, atherosclerosis, and/or lysosomal storage diseases.

The salicylanilides described herein can, in aspects, be administered for example, by parenteral, intravenous, subcutaneous, intradermal, intramuscular, intracranial, intraorbital, ophthalmic, intraventricular, intracapsular, intraspinal, intracisternal, intraperitoneal, intranasal, intrarectal, aerosol or oral administration. Typically, the salicylanilides described herein are administered orally and/or rectally.

The salicylanilides may, in aspects, be administered in combination, concurrently or sequentially, with conventional treatments for infection, including antibiotics, for example. The salicylanilides may be formulated together with such conventional treatments when appropriate. For example, the salicylanilides may be administered following conventional treatments so that the gut microbiota is restored following the disruption caused by conventional treatments.

The salicylanilides may be used in any suitable amount, but are typically provided in doses comprising from about 0.001 µM to about 1000 µM salicylanilide, such as from about 0.001 µM, about 0.01 µM, about 0.1 µM, about 1 µM, about 10 µM, or about 100 µM to about 0.01 µM, about 0.1 µM, about 1 µM, about 10 µM, about 100 µM, or about 1000 µM salicylanilide. Alternatively, the salicylanilides may be administered in doses such as from about 0.001 mg/kg to about 1000 mg/kg, such as from about 0.001 mg/kg, about 0.01 mg/kg, about 0.1 mg/kg, about 1 mg/kg, about 10 mg/kg, or about 100 mg/kg to about 0.01 mg/kg, about 0.1 mg/kg, about 1 mg/kg, about 10 mg/kg, about 100 mg/kg, or about 1000 mg/kg. Typically, the dose chosen is below the threshold that could negatively disrupt the gut microbiota and/or is below the threshold above which bactericidal effects (on *C. difficile* and/or beneficial gut microbiota) may be observed.

Additionally, treatment with the salicylanilides described herein may occur once or may be repeated several times. For example, treatment may occur daily, weekly, monthly, yearly, or a combination thereof, depending upon the disease state. For example, a subject may be administered several doses on an hourly, daily, or weekly basis in order to treat an active infection. Once the infection slows or goes into remission, follow-up maintenance doses may be provided, for example, on a daily, weekly, or monthly basis, every three months, every six months, or on a yearly basis, or simply as needed at the sign of any return of infection.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1—Oral Niclosamide Inhibits *C. difficile* Virulence and Prevents Disease Pathogenesis in Mice without Disrupting the Gut Microbiota Abstract

*Clostridium difficile* is the leading cause of nosocomial diarrhea and colitis in the industrialized world. Disruption of the protective gut microbiota by antibiotics enables colonization by multidrug-resistant *C. difficile*, which secrete up to three different protein toxins that are responsible for the gastrointestinal sequelae. Oral agents that inhibit the damage induced by toxins, without altering the gut microbiota, are urgently needed to prevent primary disease and break the cycle of antibiotic-induced disease recurrence. Here, we show that the anthelmintic drug, niclosamide, inhibits the pathogenesis of all three toxins by targeting a host process required for entry into colonocytes by each toxin. In mice infected with an epidemic strain of *C. difficile*, expressing all three toxins, niclosamide reduced both primary disease and recurrence, without disrupting the diversity or composition of the gut microbiota. Given its excellent safety profile, niclosamide may address an important unmet need in preventing *C. difficile* primary and recurrent diseases.

Introduction

*C. difficile* is a spore-forming Gram-positive bacterium that causes a range of gastrointestinal diseases, typically in individuals that have taken a course of broad-spectrum antibiotics, which lowers the diversity of the protective resident GI microbiota (1). In the resulting aftermath, opportunistic *C. difficile* colonizes the lower GI tract of susceptible individuals and secretes up to three gut-damaging toxins, including two large homologous toxins TcdA and TcdB, and in the case of epidemic strains of *C. difficile*—such as ribotype 027 (RT027) (2) and ribotype 078 (RT078) (3) —a third, unrelated binary toxin called CDT (4). In recent years, *C. difficile* has become a major public health concern, due to the proliferation and global spread of epidemic strains, which are associated with increased morbidity and mortality (5). The increased virulence of these strains has been attributed to several factors, including: acquisition of mutations in gyrB that result in resistance to fluoroquinolones (5); increased expression of toxins (6, 7); production of a more cytotoxic form of TcdB (8); and, expression of CDT (2).

Extensive experimental and epidemiological evidence support a role for toxins as the primary determinants of disease pathogenesis. Isogenic knockout studies, in which toxins were deleted individually, or in combination, showed that TcdA and TcdB alone are sufficient to cause fulminant disease in hamsters (9, 10), whereas CDT appears to contribute to virulence in combination with TcdA or TcdB (11). Importantly, knockout of all three toxins renders *C. difficile* completely avirulent.

The inextricable link between antibiotic-induced dysbiosis of the GI microbiota and infection by *C. difficile*, together with the well-validated role of toxins in driving disease pathogenesis, provide strong rationale and validation for targeting the actions of the *C. difficile* toxins as a novel approach to treat or prevent *C. difficile* infection (CDI). Despite early clinical setbacks with nonspecific polymers meant to sequester the toxins in the GI tract (12), the monoclonal antibody bezlotoxumab (Zinplava—Merck), which binds to and blocks TcdB following toxin-induced damage of the gut lining (13), was recently approved for use in CDI patients for reducing recurrence (14, 15). This important clinical validation of toxin-targeting approaches for treating *C. difficile* recurrence has fueled efforts to develop next-generation antitoxins that are orally-bioavailable (i.e., small molecules), have a greater spectrum of activity against all *C. difficile* toxins, and potentially be used prior to, or during a suspected primary infection. Ideally, such a therapeutic, in addition to having an impeccable safety profile in humans, would not itself affect the composition of the protective gut microbiota, which is ultimately required to prevent further re-infection. Moreover, with the emergence of new *C. difficile* ribotypes, such as RT033, that do not express TcdB, but are nevertheless pathogenic (16-20), it would be desirable to have a single agent with the above characteristics that is also able to prevent TcdA- and/or CDT-induced pathogenesis.

In this study, we screened libraries of approved drugs in a phenotypic screen of TcdB-induced cell rounding with the goal of identifying small molecules that may potentially be repurposed for treating CDI through direct toxin inhibition. Recent drug repurposing phenotypic screens have led to discoveries of potential new candidate therapies for a number of infectious diseases, including for giardiasis (21), Zika virus infection (22), Ebola virus disease (23), and Hepatitis C infection (24). Here, among the panel of hits identified that completely protected cells from TcdB intoxication, we identified niclosamide, a widely used anthelmintic drug approved by the US FDA for treating intestinal infections of tapeworms (25). Based on its excellent safety profile (26, 27), and its preferential biodistribution in the colon resulting from its poor absorption in the GI tract (26), we investigated niclosamide as an oral toxin-neutralizing treatment for CDI.

Materials and Methods
Cell Lines, Consumables, and Reagents

Plasticware used for cell culture and enzyme assays were purchased from Corning. Streptavidin Hi-bind plates, Superblock buffer, SuperSignal West, and Quantablu peroxidase substrate were purchased from Thermo Pierce (Rockford, Ill.). Cell lines CHO-k1, Vero, and IMR90 were from ATCC (Manassas, Va.). Anti-Rac1 antibody Mab102 was from BD Biosciences (Mississauga, ON), and anti-GST antibody was from Genscript (Piscataway, N.J.). Anti-mouse conjugated peroxidase antibody was from GE Healthcare (Baie d'Urfe, QC). The Spectrum library, consisting of 2320 individual compounds formatted as 10 mM solutions in DMSO, was purchased from Microsource (Gaylordsville, Conn.). The Flav500 (Timtec library) was purchased from Sigma-Aldrich (Oakville, ON).

Protein Expression and Purification

Expression and isolation of recombinant toxins was as described by Yang et al (53). Briefly, transformed *Bacillus megaterium* was inoculated into LB containing tetracycline and grown to an A600 of 0.7, followed by overnight xylose induction at 37° C. Bacterial pellets were collected, resuspended with 20 mM Tris pH 8/0.5 M NaCl, and passed twice through an EmulsiFlex C3 microfluidizer (Avestin, Ottawa, ON) at 15,000 psi, then clarified by centrifugation at 18,000 g for 20 min. TcdB was purified by nickel affinity chromatography followed by anion exchange chromatography using HisTrap FF and HiTrap Q columns (GE Healthcare, Baie D'Urfe, QC), respectively. Fractions containing TcdB were verified by SDS-PAGE, then pooled and diafiltered with a 100,000 MWCO ultrafiltration device (Corning) into 20 mM Tris PH 7.5/150 mM NaCl. Finally, glycerol was added to 15% v/v, the protein concentration was estimated by A280 (using coefficient 288160), divided into single use aliquots, and stored at −80° C. Cell lysates were prepared as described for full-length TcdB, and purification of the protein was by nickel affinity chromatography using HisTrap FF columns.

The pGEX-Rac1 plasmid (Addgene plasmid 12200) for expression of GST-Rac1 protein was previously described by Bagrodia et al (54) and obtained from Addgene (Cambridge, Mass.). The plasmid was transformed into *E. coli* BL21 DE3, and recombinant protein expression was achieved by induction of the culture with 0.1 mM IPTG for 5 hours at 30° C. The cell pellet was recovered by centrifugation, resuspended with 5 mL/g of pellet in 20 mM Tris 7.5/150 mM NaCl, and sonicated. The cell lysate was clarified by centrifugation, and the GST fusion protein was purified by chromatography through a GSTrap Fast Flow column (GE Healthcare, Baie D'Urfe, QC). Following elution with 10 mM glutathione, fractions containing purified protein were pooled and stored at −80° C. in the presence of 15% v/v glycerol.

Arrayscan High Content Phenotypic Screen

IMR90 cells were grown in EMEM (Wisent) supplemented with 10% FBS and penicillin-streptomycin (complete EMEM) and were seeded in 96-well Cellbind plates (Corning) at a density of 8,000-10,000 cells/well. The next day, the media was exchanged with serum free EMEM (SFM) containing 1 μM Celltracker Orange CMRA (Molecular Probes). After 60 minutes, excess dye was removed by media exchange with SFM. An Agilent Bravo liquid handler was used to deliver 0.4 μL of compound from the Microsource library plate to the cell plate, immediately followed by 10 μL of 100 μM TcdB (diluted in SFM) to a final volume of 100 μL, representing a concentration of toxin previously established as ~EC99 levels of cytopathology. The cell plates were returned to the incubator for 3.5 h before imaging. Celltracker-labelled cells were evaluated on a Cellomics ArrayScan VTI HCS reader (Thermo Scientific, Waltham, Mass.) using the Target Acquisition mode, a 10× objective and a sample rate of 100 objects per well. After recording all image data, the cell rounding and shrinking effects of TcdB intoxication were calculated using the cell rounding index (CRI), a combined measure of the length to width ratio (LWR) and area parameters. The % inhibition was calculated as the ratio between the sample well and the average toxin-untreated controls after subtracting the average DMSO control values. The Z' value was calculated using the equation $Z'=1-[(3s_f+3s_b)/(\mu_b-\mu_f)]$, where s=standard deviation, μ=average, f=DMSO control, and b=toxin-untreated control. Wells which displayed potential suppression of toxin activity (>39%) were verified by visual inspection to immediately exclude false hits arising from cellular toxicity, precipitation, or auto-fluorescence/quenching. Hits for confirmation and follow-up assays were ordered from Microsource and Sigma as lyophilized powders. Dose response curves were created and evaluated using Prism software (Graphpad Software, La Jolla, Ca).

Acute Toxicity Assay

Loss of cellular ATP as a marker of high dose (1 nM) TcdB toxicity was measured as described for the Arrayscan screen protocol, except that CellTiter-Glo reagent (Promega, Madison, Wis.) was added to the cells 3 h post toxin challenge, and luminescence was recorded on a Spectramax M5 plate reader.

Lysotracker Assay

Endosomal pH neutralization was assayed essentially as described by Slater et al. (55); IMR90 cells in complete EMEM were plated at 14,000 cells/well (~95% confluency). After 24 h the media was changed to SFM for 60 minutes, then compound was added to 40 μM and incubated at 37° C.

for 2 h. Lysotracker red DND-99 and Hoechst (Life Technologies) were added to 0.1 µM and 1 µM, respectively, and incubated for 60 minutes. Excess dye was removed by media change and the fluorescence at ex/em 574/594 was read on an Envision plate reader (Perkin Elmer). Representative cell images were taken using a Zeiss Axiovert fluorescence microscope using DAPI and Texas Red filters to visualize the Hoechst and Lysotracker staining, respectively.

Cysteine Protease Assay

Inhibition of TcdB self-cleavage by its intrinsic cysteine protease activity was measured by pre-incubating test compounds with TcdB for 30 min, followed by addition of InsP6 and incubating the reaction at 37° C. for 3 h. Cleavage was visualized by electrophoresing the samples on SDS polyacrylamide gels and staining with Coomassie Blue R250.

Glucosyltransferase Western Blot Assays

For each reaction containing 10 nM GTD and 25 µM UDP-glucose, compound was added (1% final DMSO) and preincubated 30 minutes, followed by addition of gstRac1 to 0.8 µM. The reaction was stopped after a 60 min reaction time with an equal volume of Laemmli loading buffer plus β-mercaptoethanol (Bio-Rad, Mississauga. ON), heated to 90° C. before immediately loading on an SDS polyacrylamide gel. Following electrophoresis, samples were transferred to nitrocellulose using an iBlot device (Invitrogen), blocked with 5% milk/TBS, and probed with a 1/1000 dilution of either Mab102 or anti-GST antibodies. Following an overnight incubation with the primary antibody, the blot was washed with TBS/0.1% Tween20 and incubated with a 1/5000 dilution of anti-mouse horseradish peroxidase for 60 min. After the final washes in TBST, chemiluminescent detection was carried out using Supersignal substrate (Thermo Pierce) and exposing to Biomax MR film (Kodak, Rochester, N.H.).

Differential Scanning Fluorometry

DSF was performed in a similar manner as described previously(56). TcdB protein was diluted in phosphate buffer (100 mM KPO4, 150 mM NaCl, pH 7) containing 5×SYPRO Orange (Invitrogen, Burlington, ON) and a serial dilution of test compound. A Biorad CFX96 qRT-PCR thermocycler was used to establish a temperature gradient from 15° C. to 95° C. in 30 s increments, while simultaneously recording the increase in SYPRO Orange fluorescence as a consequence of binding to hydrophobic regions exposed on unfolded proteins. The Bio-Rad CFX Manager 3.1 software was used to integrate the fluorescence curves to calculate the melting point.

TcdB Cell Surface Binding

TcdB binding to Vero cells was assessed as described earlier with minor modifications(57). Briefly, 100 ng/ml TcdB was pre-incubated with 40 µM methyl cholate or 40 µM niclosamide or NEN for 45 minutes in Eagle's MEM supplemented with 10% FBS, 100 U/ml penicillin and 100 U/ml streptomycin. Mixtures were then added to confluent cultures of pre-chilled Vero cells and plates were incubated on ice for 45 min. Plates were then washed 3 times with cold PBS and harvested by scraping. Membranes were isolated, and samples analyzed by Western blot as previously described (57).

Scintillation Proximity Assay (SPA)

The TcdB glucosyltransferase domain (GTD) was incubated at a final concentration of 2 nM in glucosylation buffer (50 mM HEPES pH 7.5, 100 mM KCl, 4 mM $MgCl_2$, 1 mM $MnCl_2$) with various concentrations of inhibitor in a final volume of 20 µl in a 96-well PCR plate (Sarstedt). Reactions were started with the simultaneous addition of 2.5 µl each of GST-Rac1 (20 µM final) and a mixture of 0.5 µCi of UDP-[6 $^3$H]-glucose (0.5 µM final) and cold UDP-glucose (19.5 µM final). Reactions were allowed to proceed at room temperature for 30 min, before being transferred to a white, polystyrene 96-well plate (Costar) containing a mixture of 250 µl of 0.5 M EDTA and glutathione-coated PVT beads (PerkinElmer) at a final concentration of 2 mg/ml. The beads were allowed to settle overnight at room temperature to increase the signal to background ratio before being analyzed on a TopCount NXT scintillation counter (PerkinElmer). Results were analyzed using GraphPad Prism 5.0.

UDP-Glo™ UDP-Glucose Hydrolase Assay (Promega)

Experiments were performed as per the manufacturer's instructions. Briefly, 100 nM of GTD enzyme was incubated in glucosylation buffer (see above) with various concentrations of inhibitor in a final volume of 16 µl. Reactions were started with the addition of 4 µl of UDP-glucose (50 µM final). Reactions were allowed to proceed at room temperature for 15 minutes. To stop the reaction, 10 µl were removed and added to a white, polystyrene 96-well half-area plate (Costar) containing 10 µl of UDP detection reagent. Plates were incubated at room temperature for 1 h, then luminescence was recorded on a SpectraMax M5e plate reader (Molecular Devices) with an integration time of 750 ms. Results were analyzed with SoftMax Pro 6.2.2 and GraphPad Prism 5.0.

Anaerobic Agar Dilution Assays to Determine Effects of NEN on *C. difficile* Strains NEN and comparator antibiotics were prepared on the day of testing using solvents recommended by CLSI. Stock solutions of all compounds were made at 100× the final testing concentration. Test organisms consisted of clinical isolates from the American Type Culture Collection (ATCC) and Micromyx repository. Drug dilutions and drug-supplemented agar plates were prepared manually. After pouring the Supplemented *Brucella* agar plates, they were allowed to dry, pre-reduced in the Bactron II anaerobic chamber, then spot-inoculated using a Steers Replicator, yielding a final cell concentration on the surface of the agar plates of ~1×10$^4$ colony-forming units/spot. After the inocula had dried, the drug-supplemented plates were incubated at 35° C. for 16 h, 24 h, 32 h and 48 h under anaerobic conditions. The MIC was read per CLSI guidelines as the concentration at which growth was significantly inhibited relative to the growth control.

Microbiota Analysis

DNA was extracted using the MagAttract PowerMicrobiome DNA/RNA kit (Qiagen) from the fecal pellet of all samples. Briefly, the glass bead plate was used to mix fecal material and lysis solution, and inhibitor was subsequently removed from the supernatant. ClearMag Beads suspension was then mixed with 450 ul of the supernatant to purify the extracted DNA. DNA was extracted from all samples (150 mg) using the MagAttract PowerMicrobiome DNA/RNA kit (Qiagen) implemented on a Hamilton STAR robotic platform and after a bead-beating step on a TissueLyzer II (Qiagen) in 96-deep well plates. PCR amplification of the 16S rRNA gene V4 hypervariable region was performed using dual-barcoded universal primers 515F and 806R as previously described(58). High-throughput sequencing of the amplicons was performed on an Illumina MiSeq platform using the 300 bp paired-end protocol. Raw data was demultiplexed using the idemp tool (59). Barcode, adapter and primer sequences were trimmed using tagcleaner (60). Quality assessment and sequencing error correction was performed using the software package DADA2(61) and the following parameters: forward reads were truncated at position 220 and the reverse reads at position 160 based on the sequencing quality plot, no ambiguous based and a maximum of 2 expected errors per-read were allowed(62). The quality-trimmed reads were used to infer ribosomal sequence variants and their relative abundance in each sample after removing chimera. A total of 205 fecal samples were characterized resulting in a total of 6,619,465 high-quality non-chimeric amplicon sequences, corresponding to 32,290 (±19,999) sequences per samples. The GreenGene database version 13.8(63) was used for taxonomic classification. Within-sample diversity was estimated using Shannon diversity index(64). Inter-community comparative analyses were performed using NMDS (nonmetric dimensional scaling) based on Bray-Curtis distance metrics and were plotted using software package phyloseq (65). Linear discriminant analysis (LDA) effect size (LEfSe) analysis (38) was applied to identify bacterial phylotypes with relative abundance statistically different between control and NEN (50 mg/kg) treatments. The alpha value for the non-parametric factorial Kruskal-Wallis (KW) sum-rank test(66) was 0.05 and the threshold for the logarithmic LDA model (67) score for discriminative features was set at 2.0.

Data Deposition

All 16S rRNA sequence data were deposited in SRA under BioProject PRJNA423011 (SRP128045).

Results

High-Throughput Phenotypic Screen for Inhibitors of TcdB-Induced Cell Rounding

Intoxication by TcdB toxin is a multistep process, involving four functionally-distinct toxin domains, and several host-factors and processes (FIG. 1a). Intoxication of cells leads first to cytopathic effects (i.e., rounding of cells) (28) within 1-3 h, and later, cytotoxic effects (i.e., apoptosis) after 24 h (29). To identify small molecules that protected cells from TcdB, we employed a high-throughput assay of TcdB-induced cell rounding that we previously developed, which quantifies the extent of rounding of human lung fibroblasts treated with cytopathic doses of TcdB (i.e., 1 μM for 3 h) using high-content imaging analysis (30). To increase the probability of identifying compounds with suitable properties for subsequent in vivo studies and beyond, we screened the Library of Pharmacologically Active Compounds (1,280 compounds) and the Microsource Library Spectrum Collection (2,360 compounds) —libraries consisting of approved drugs and pharmacologically active molecules with known targets and pharmacological properties.

Figure 10:
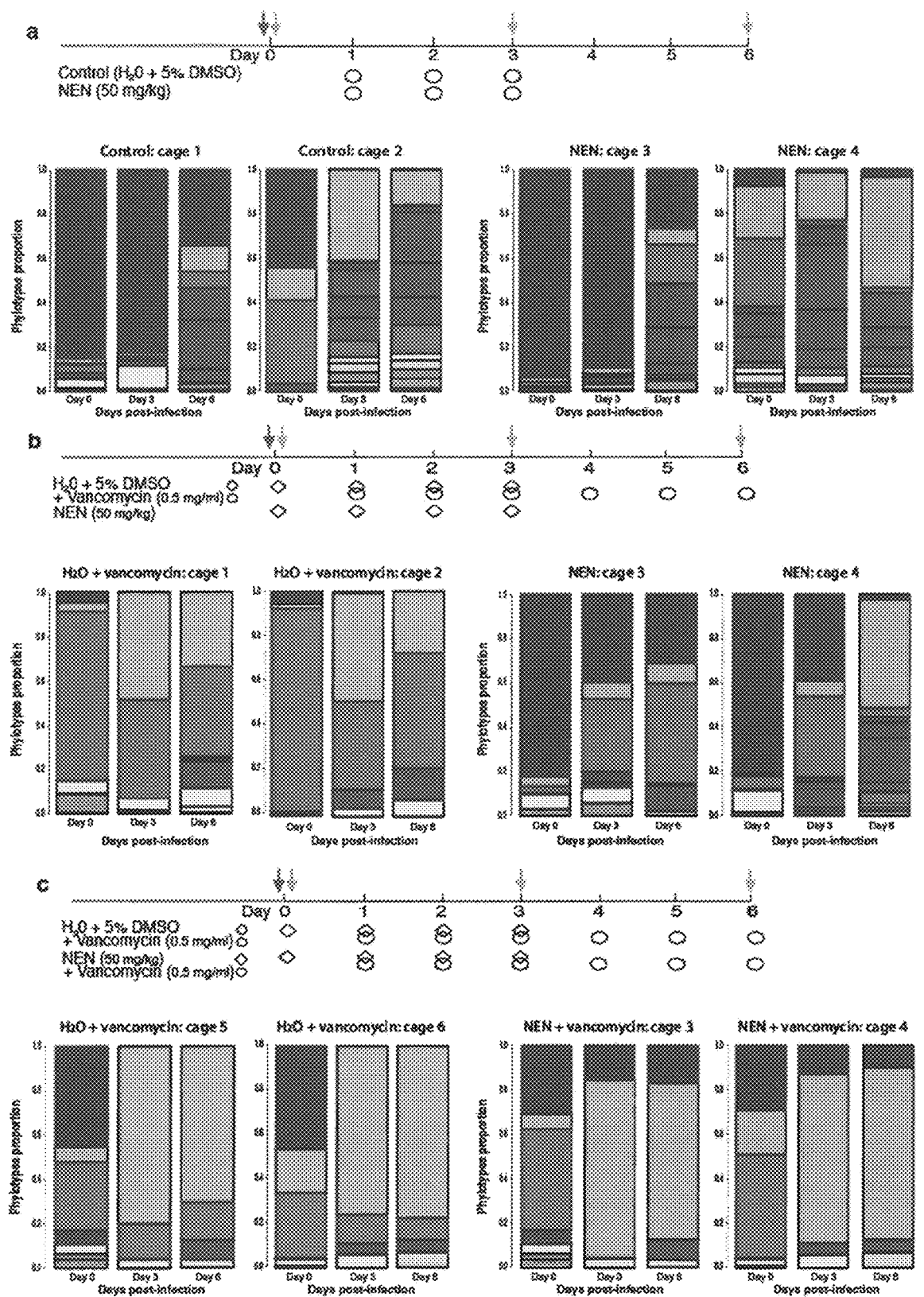
FIG. 10. Effect of treatment on the composition of the gut microbiota by cage for each treatment group. Experimental design is shown on top panel. Each barplot indicates the mean relative abundance of bacterial families with relative abundance >1%. (a) control (water with 5% DSMO) and NEN treatment (50 mg/kg); (b) water with vancomycin and NEN treatment (50 mg/kg); (c) water with vancomycin and NEN treatment (50 mg/ml) with vancomycin (0.5 mg/ml). First sampling day (day 0) is 4 hours after *C. difficile* infection.

From the 60 compounds that protected cells from TcdB by greater than the statistical cut-off of three standard deviations of the mean of the data (FIG. 5), we triaged drugs with undesirable mechanisms-of-action (i.e., antibiotics and antiseptics), and those that are known to be toxic or poorly tolerated in humans. Emerging from this prioritization were the three related salicylanilide anthelmintic drugs: niclosamide (71% inhibition), closantel (60% inhibition) and oxyclozanide (43% inhibition) (FIG. 1b, c); drugs that act on parasites within the GI lumen, and that have well-documented safety margins in humans. Among these salicylanilide, niclosamide was the most potent inhibitor of TcdB-induced cell-rounding, protecting cells with an $EC_{50}=0.51\pm0.03$ μM (FIG. 1d). Protection from TcdB-induced cell-rounding by niclosamide was complete; human IMR-90 fibroblasts that were co-incubated with niclosamide and TcdB were indistinguishable from cells that had not received toxin (FIG. 1e). To evaluate the extent of protection by niclosamide against different amounts of TcdB (reflecting the range of toxin levels that might be experienced during an infection), cells were treated with a range of TcdB concentrations at different fixed doses of niclosamide. In the absence of drug, TcdB dose-dependently induces cell rounding with an $EC50=0.8$ μM (FIG. 10. In the presence of increasing concentrations of niclosamide, the amount of TcdB required to reach equivalent levels of rounding increased dramatically. Remarkably, above the EC50 of niclosamide, cells were completely protected from TcdB by over three orders-of-magnitude, corresponding to a protection factor (PF) >5000 (FIG. 1f).

Next, we tested the ability of niclosamide and the more water-soluble ethanolamine salt form of niclosamide, niclosamide ethanolamine (NEN)(26) to maintain the integrity of human epithelial colorectal cells (CaCo-2 cells) that were treated with TcdB. Treatment of a confluent monolayer of CaCo-2 cells with TcdB results in disruption of monolayer integrity and loss of trans-epithelial resistance (31) within hours of application as a result of GTD-induced actin depolymerization. Disruption of the monolayer integrity by TcdB was prevented by co-treatment with niclosamide (FIG. 6). Furthermore, NEN prevented the TcdB-induced disruption of Caco-2 monolayers maintaining barrier function to untreated levels (FIG. 1g).

Mechanism of TcdB Neutralization by Niclosamide

Figure 2:
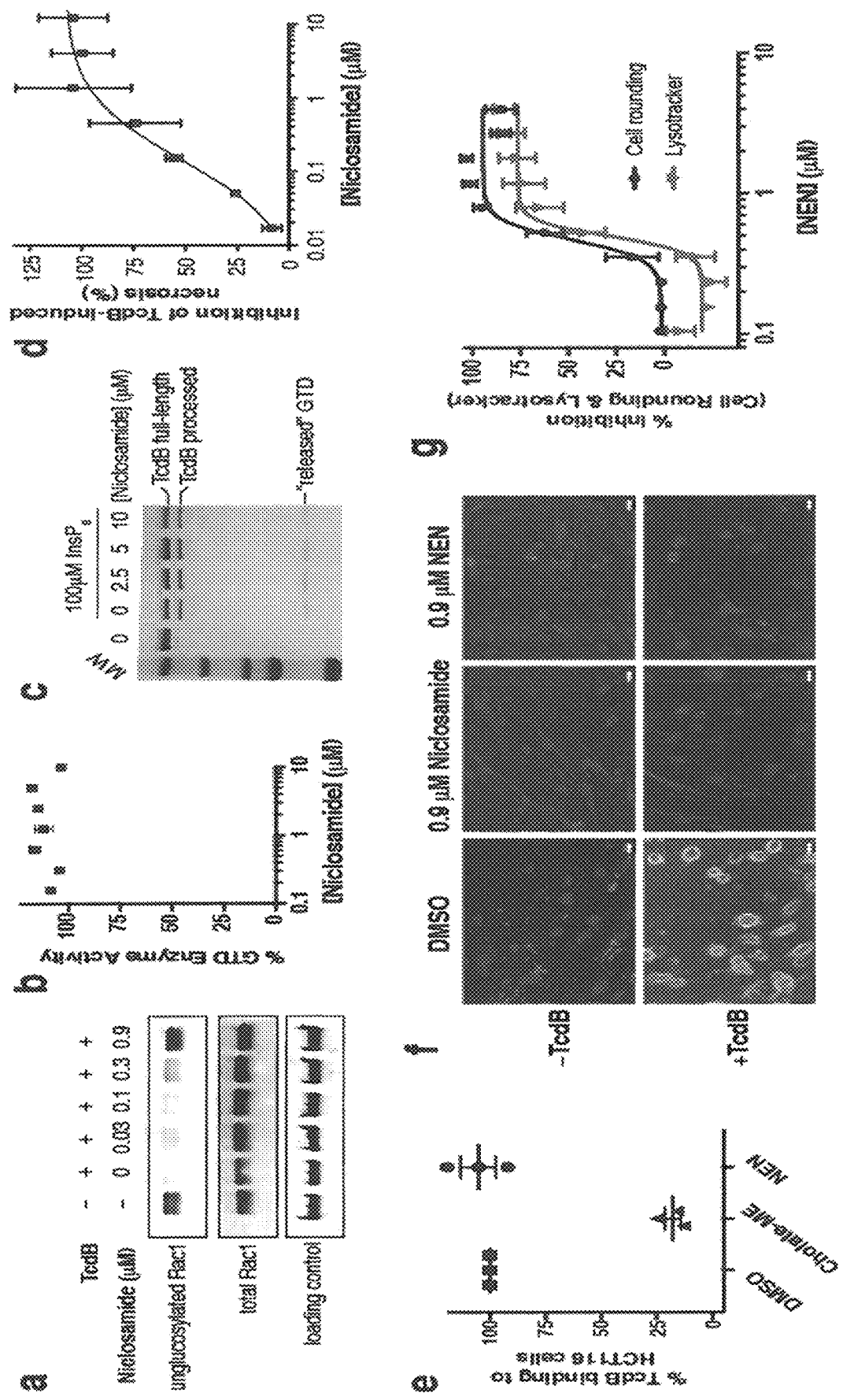
FIG. 2. Determination of the mechanism-of-action of niclosamide inhibition of TcdB intoxication. (a) Representative Western blot image for intracellular Rac1 glucosylation. IMR-90 cells were treated with doses of niclosamide (shown) for 15 min, followed by treatment with 0.5 µM TcdB. Cells were harvested in lysis buffer 1 h later and processed for Western blot as described in Online Methods. Mab102, which recognizes un-glucosylated Rac1 in cells, shows a dose-dependent re-appearance, relative to total Rac1 levels (n=2). (b) In vitro GTD glucosyltransferase assay. Recombinant GTD was incubated for 30 minutes with different doses of niclosamide (n=3). Activity was measured as described in the Online Methods. (c) In vitro auto-processing assay.

To elucidate the mechanism by which niclosamide inhibits TcdB-induced cell rounding, we carried out a series of assays that evaluate each step of the intoxication pathway in isolation (FIG. 1a). Though niclosamide dose-dependently inhibits Rac1 glucosylation in cells (FIG. 2a), no direct inhibition of GTD enzymatic activity is observed in vitro up to 10 μM niclosamide, indicating that inhibition occurs at a step upstream of Rac1 glucosylation (FIG. 2b). Release of GTD by the APD domain, the step immediately preceding Rac1 glucosylation, was also unaffected by up to 10 μM niclosamide in an in vitro assay of inositol hexakisphosphate-induced autoprocessing (FIG. 2c).

Figure 7:
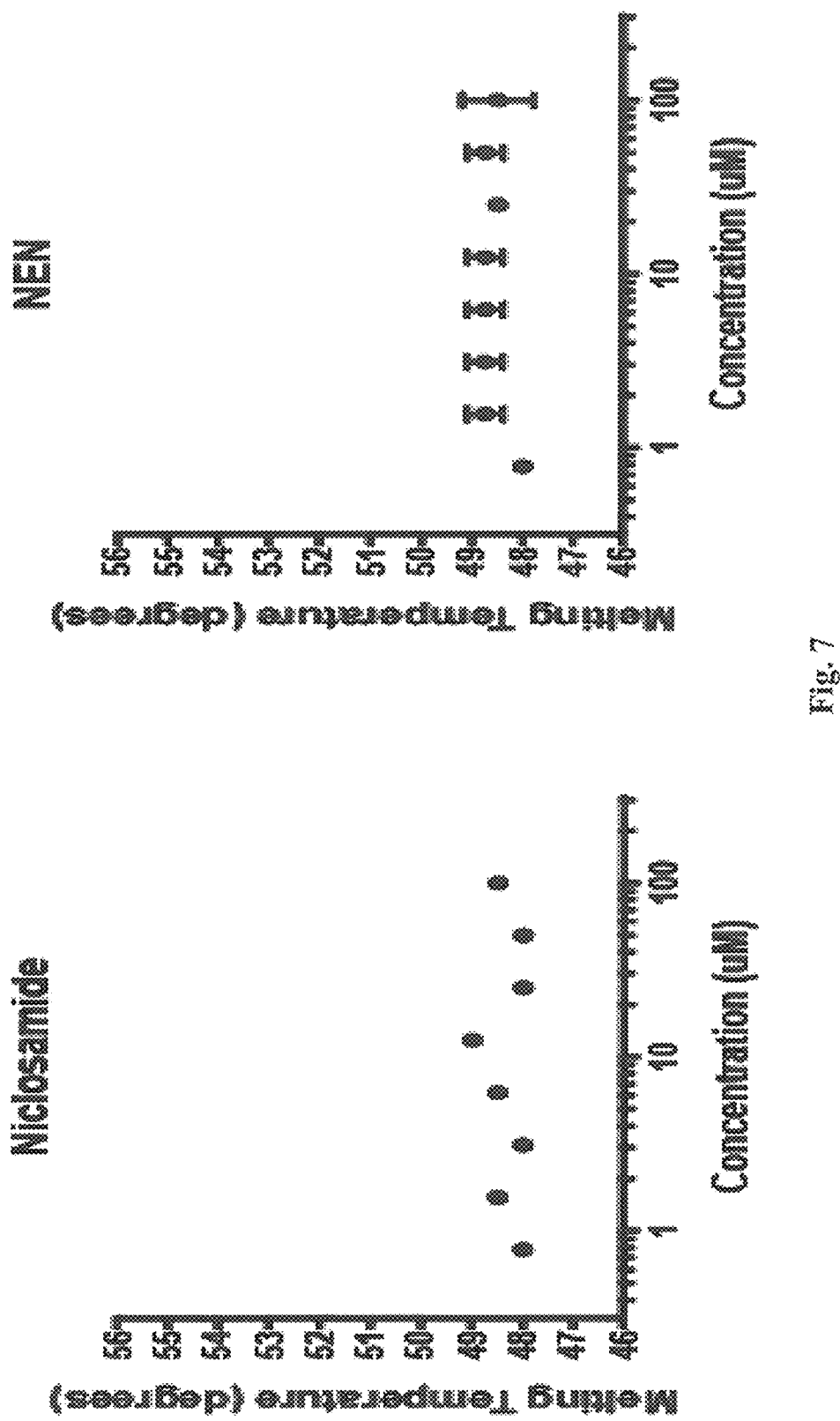
FIG. 7. Thermal stability of TcdB in the presence of niclosamide and NEN.

Consistent with niclosamide not acting through inhibition of either GTD or APD activity, we found that niclosamide inhibited TcdB-induced necrosis (FIG. 2d) —a cellular phenotype that is independent of GTD and APD activity, but dependent on cell-surface binding, uptake into endosomes, and pH-dependent pore-formation in endosomes for full activity (32, 33). Using mammalian cells expressing all three known receptors, we found that niclosamide did not affect TcdB binding to the cell surface (FIG. 2e). Moreover, we saw no evidence for a direct binding interaction between niclosamide and TcdB (FIG. 7). Taken together, these data point to niclosamide acting on the host, and through inhibition of the pore-formation process. Niclosamide has been reported to mildly increase the pH of endosomes through a unique 'proton-shuttle' mechanism, which is distinct from other modes of endosomal deacidification, such as lysosomotropism. Using fluorescent Lysotracker dye, a lysosomotropic molecule that accumulates and fluoresces in acidic vesicles, we found that pre-treating cells with either niclosamide or NEN indeed reduces Lysotracker fluorescent staining, consistent with these molecules increasing the pH of endosomal compartments (FIG. 2f). Importantly, the dose-dependent increase in endosomal pH by niclosamide and NEN overlapped with the dose-titration curves for inhibition of cell rounding and necrosis (FIG. 2g).

Niclosamide Protects Cells from all Three C. difficile Toxins

The determination that niclosamide inhibited TcdB at the level of the host endosome prompted us to consider the intriguing possibility that niclosamide might additionally block the actions of TcdA and CDT, both of which require endosomal acidification for pore-formation and intracellular entry. Indeed, niclosamide and NEN completely protected cells from TcdA-induced cell rounding, and from CDT-induced damage (i.e., depolymerization of the actin cytoskeleton), at the same doses that protect cells from TcdB (Table 1 and FIG. 8). NEN also protected cells against a form of TcdB derived from hypervirulent strains of *C. difficile*, which have been shown to enter cells at an earlier stage in endocytosis (8) (Table 1).

TABLE 1

Inhibition of *C. difficile* toxin-induced cytotoxicity by niclosamide and NEN.

| | $TcdB_{012}$ | $TcdB_{078}$ | $TcdB_{027}$ | TcdA | CDT |
|---|---|---|---|---|---|
| Niclosamide $IC_{50}$ (μM) | 0.44 ± 0.05 | 0.5 ± 0.2 | 0.4 ± 0.1 | 0.5 ± 0.1 | 0.53 ± 0.08 |
| NEN $IC_{50}$ (μM) | 0.43 ± 0.03 | 0.45 ± 0.09 | 0.5 ± 0.1 | 0.55 ± 0.08 | 0.50 ± 0.09 |

The data are expressed as the means ± s.d.
Niclosamide replicates: $TcdB_{012}$, n = 8; $TcdB_{078}$, n = 4; $TcdB_{027}$, n = 4; TcdA, n = 6; CDT, n = 4
NEN replicates: $TcdB_{012}$, n = 7; $TcdB_{078}$, n = 4; $TcdB_{027}$, n = 3; TcdA, n = 4; CDT, n = 3

Demonstrating protection against CDT, a toxin that bears no structural or functional similarities to TcdA and TcdB, other than requiring low pH to escape endosomes, further supports the mechanism-of-action for niclosamide. More importantly, this finding suggests that niclosamide, as a single entity, could potentially protect from infection and disease by all pathogenic *C. difficile* strains, expressing any combination of toxins, in vivo.

Figure 3:
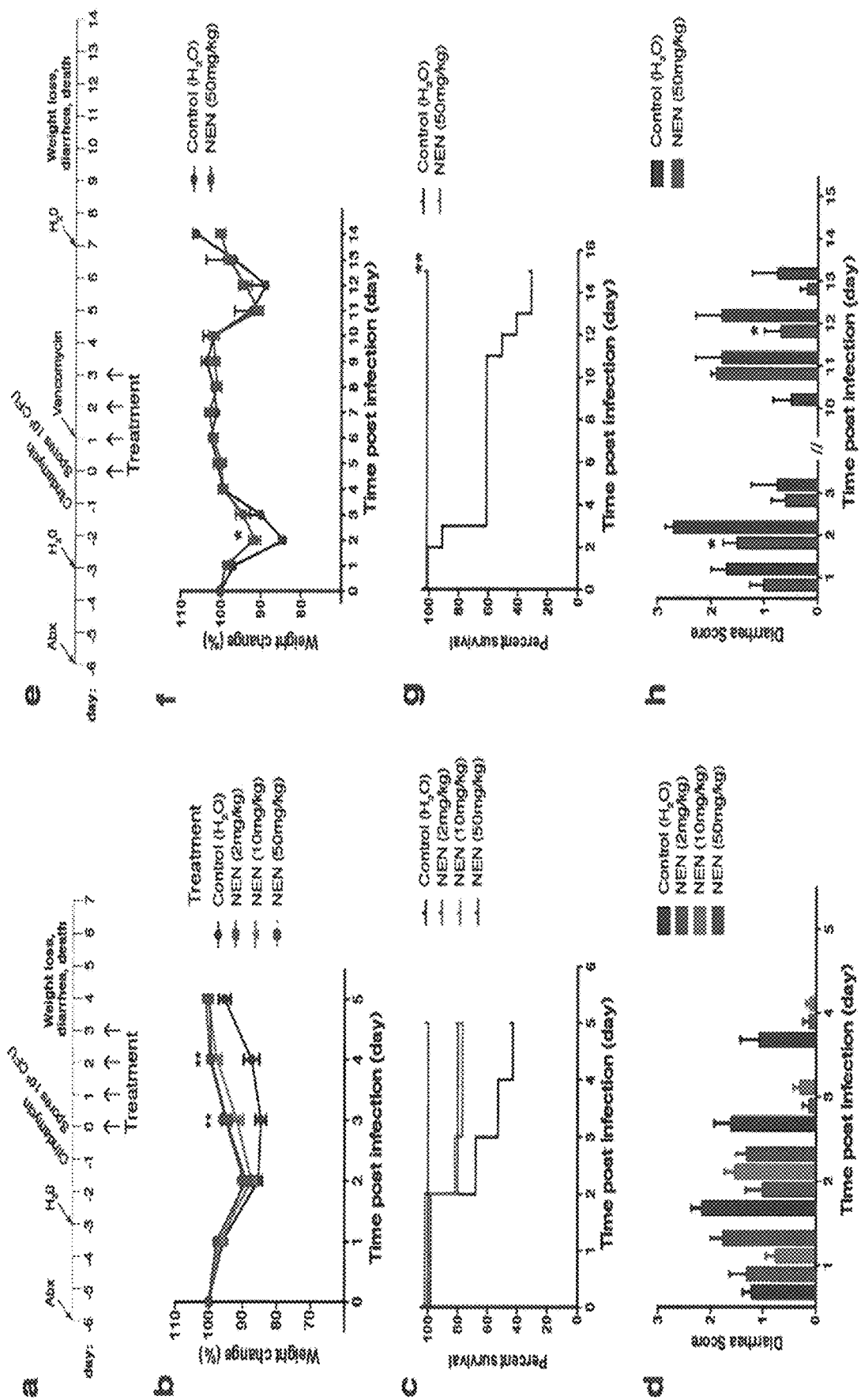
FIG. 3. Niclosamide ethanolamine (NEN) is protective in primary and recurrent CDI. (A) Weights of mice after challenge with *C. difficile* spores ($10^5$ CFU/mL) on day 0. Mice were treated with NEN at different doses (2, 10, and 50 mg/kg). Each point is the mean SE from day 0. (B) Mouse survival as determined by a log-rank/Mantel-Cox test. (C) Diarrhea score of infected mice[5]. (D) Weights of mice after *C. difficile* spore challenge (Day 0) followed with vancomycin in their drinking water for recurrence CDI model. (E) Survival of infected mice treated and un-treated with NEN (50 mg/kg). (F) Diarrhea score of infected mice. Data represent 10 mice/group.

NEN Reduces the Pathology Induced by an Epidemic Strain of *C. difficile* in Mice Mice preconditioned with antibiotics and challenged with *C. difficile* develop typical CDI (weight loss, diarrhea, death) in the absence of any therapeutic countermeasures (1). To test the hypothesis that niclosamide is capable of preventing disease induced by strains expressing multiple toxins, we evaluated the efficacy of NEN in protecting against CDI in a murine model challenged with the hypervirulent strain UK1 (RT027), which expresses TcdA, TcdB and CDT. Infected mice were treated with either water (control) or NEN (at different doses; 2, 10 and 50 mg/kg) via oral gavage 4 h post spore challenge and for 3 consecutive days after spore challenge (FIG. 3a). Typical symptoms of CDI in murine model include severe weight loss on days 2 and 3 post-challenge accompanied with diarrhea and high mortality rate in sham groups. All doses of NEN tested significantly protected mice from weight loss compared to control group (FIG. 3b). NEN protected mice from death in a dose dependent manner, with all mice in the 50 mg/kg group remarkably surviving infection, compared to only 45% for control group (FIG. 3c). These results closely tracked the wet tail and diarrhea scores, which were significantly lower in NEN-treated groups (FIG. 3d).

Symptomatic recurrence of CDI, which occurs in approximately one-in-four individuals, is a characteristic feature of CDI that complicates eradication and management of *C. difficile* (2). We assessed whether NEN (50 mg/kg) could prevent recurrence in a mouse model of recurrent CDI in which infected mice are treated with vancomycin (0.5 mg/mL) in their drinking water starting on day 1 ongoing for 7 days after spore challenge (FIG. 3e). NEN treatment was given via oral gavage 4 h post spore challenge and for 3 consecutive days after spore challenge. Both groups (NEN-treated and un-treated) started losing weight on day 4 after receiving vancomycin water (i.e. day 11 post spore challenge) (FIG. 3f). As above, all mice in the NEN group survived from *C. difficile* challenge, whereas more than 60% of mice in the control group became moribund (FIG. 3g,h). After resolution of symptoms, both groups began to lose weight at day 11; however, NEN-treated mice displayed less severe diarrhea scores, and importantly all NEN-treated mice survived recurrence.

NEN does not Affect *C. difficile* Growth In Vitro

As salicylanilide derivatives have been reported previously to have antimicrobial activity against certain Gram-positive bacteria (34, 35), we next carried out a series of experiments to address, whether NEN, specifically, had any antibacterial activity against *C. difficile* that may have contributed to the protective effects seen in vivo. To this end, we measured the minimum inhibitory concentrations (MICs) of NEN on individual strains of *Clostridium* species using the gold-standard anaerobic agar dilution assay (36). No antimicrobial activity was seen for NEN up to 19 μg/mL (i.e., 50 μM NEN) against either of the two strains of *C. difficile* tested (017 and 027), or against the two non-pathogenic *Clostridium* species tested (Table 2). These results were confirmed against a larger panel of *C. difficile* strains, where we saw no activity for NEN up to 32 μg/ml (i.e., 84 μM) (Table 3). While these data indicate that NEN does not affect *C. difficile* growth directly, an important feature to demonstrate for NEN, or any would-be *C. difficile* therapeutic, is the lack of effect on the gut microbiota.

TABLE 2

MIC values for Niclosamide, NEN and Vancomycin on Clostridial species

| Organism (strain) | Vancomycin (μg/mL) | NEN* (μg/mL) |
|---|---|---|
| *C. difficile* R20291 (027) | 1 | >19 |
| *C. difficile* M68 (017) | 2 | >19 |
| *C. clostridioforme* ATCC25537 | 4 | >19 |
| *C. sporogenes* ATCC3584 | 8 | >19 |

Data are n = 3
*19 μg/ml = 50 μM

TABLE 3

*C. difficile* MIC values for NEN, Vancomycin, Metronidazole and Fidaxomicin

| Organism | MIC in μg/mL | | | |
|---|---|---|---|---|
| ATCC (MMX No.)[1] | Fidaxomicin | Vancomycin | Metronidazole | NEN |
| *C. difficile* 70005 (4381) | 0.06[4] | 4[2] | 0.5[3] | >32 |
| *C. difficile* (8261) | 0.06 | 2 | 0.5 | >32 |
| *C. difficile* (8262) | 0.12 | 4 | 0.25 | >32 |
| *C. difficile* (8263) | 0.06 | 2 | 0.25 | >32 |
| *C. difficile* (8341) | 0.06 | 1 | 0.25 | >32 |
| *C. difficile* (8336) | 0.12 | 4 | 0.5 | >32 |
| *C. difficile* (8337) | 0.06 | 1 | 0.25 | >32 |

TABLE 3-continued

C. difficile MIC values for NEN, Vancomycin, Metronidazole and Fidaxomicin

| Organism | MIC in μg/mL | | | |
|---|---|---|---|---|
| ATCC (MMX No.)[1] | Fidaxomicin | Vancomycin | Metronidazole | NEN |
| C. difficile (8338) | 0.12 | 4 | 2 | >32 |
| C. difficile (8339) | 0.12 | 4 | 4 | >32 |
| C. difficile (8340) | 0.12 | 2 | 0.5 | >32 |

[1]Micromyx Isolate Number
[2]CLSI QC range (0.5-4)
[3]CLSI QC range (0.125-0.5)
[4]CLSI QC range (0.06-0.25)

NEN Effects on the Gut Microbiota In Vivo

To directly address whether NEN had any effects on the gut microbiota that may contribute to disease pathogenesis we next evaluated the effect of NEN treatment on the composition and structure of the gut microbiota in mice under various situations. First, in mice that were not infected with C. difficile, we investigated the effects of NEN at the highest dose tested in the efficacy study (i.e., 50 mg/kg), and compared this with both vancomycin and vehicle control. As shown in FIG. 4a, NEN treatment did not affect the high diversity, composition, or structure (FIG. 9) of the gut microbiota compared to vehicle control, whereas vancomycin treatment dramatically lowered the diversity of the microbiota, shifting the composition to high relative abundance of Lactobacillaceae and Enterobacteriaceae (FIG. 4a) as seen previously (37).

Figure 9:
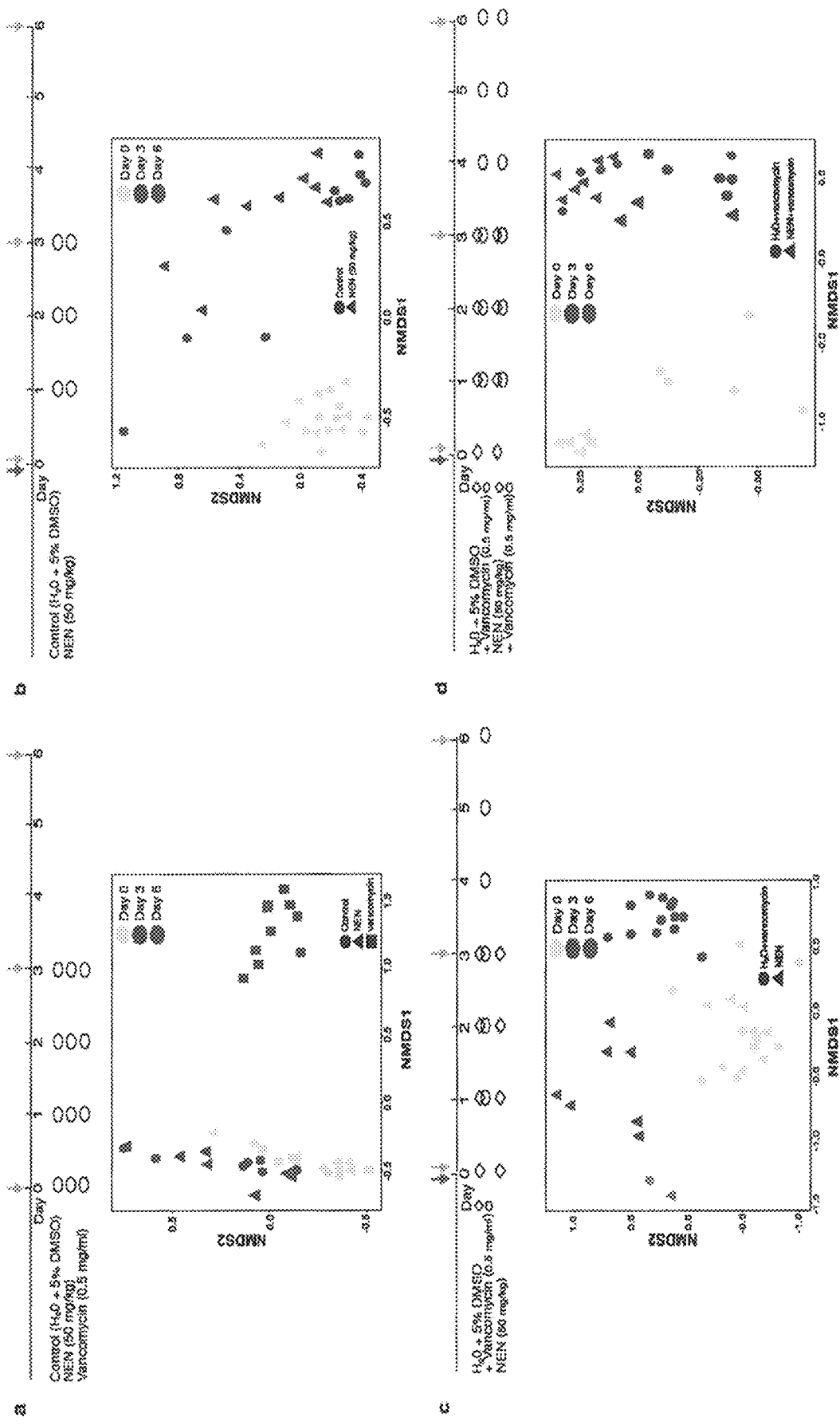
FIG. 9. Effect of treatment on the structure of the gut microbiota. Experimental design is shown on top panel. Inter-sample analyses were performed using NMDS (non-metric dimensional scaling) based on Bray-Curtis distance metrics. (a) control, NEN, and vancomycin treatment in the absence of *C. difficile* infection; (b) control (water with 5% DSMO) and NEN treatment (50 mg/kg); (c) water with vancomycin and NEN treatment (50 mg/kg); (d) water with vancomycin and NEN treatment (50 mg/ml) with vancomycin (0.5 mg/ml). First sampling day (day 0) is 4 hours after *C. difficile* infection.
Figure 11:
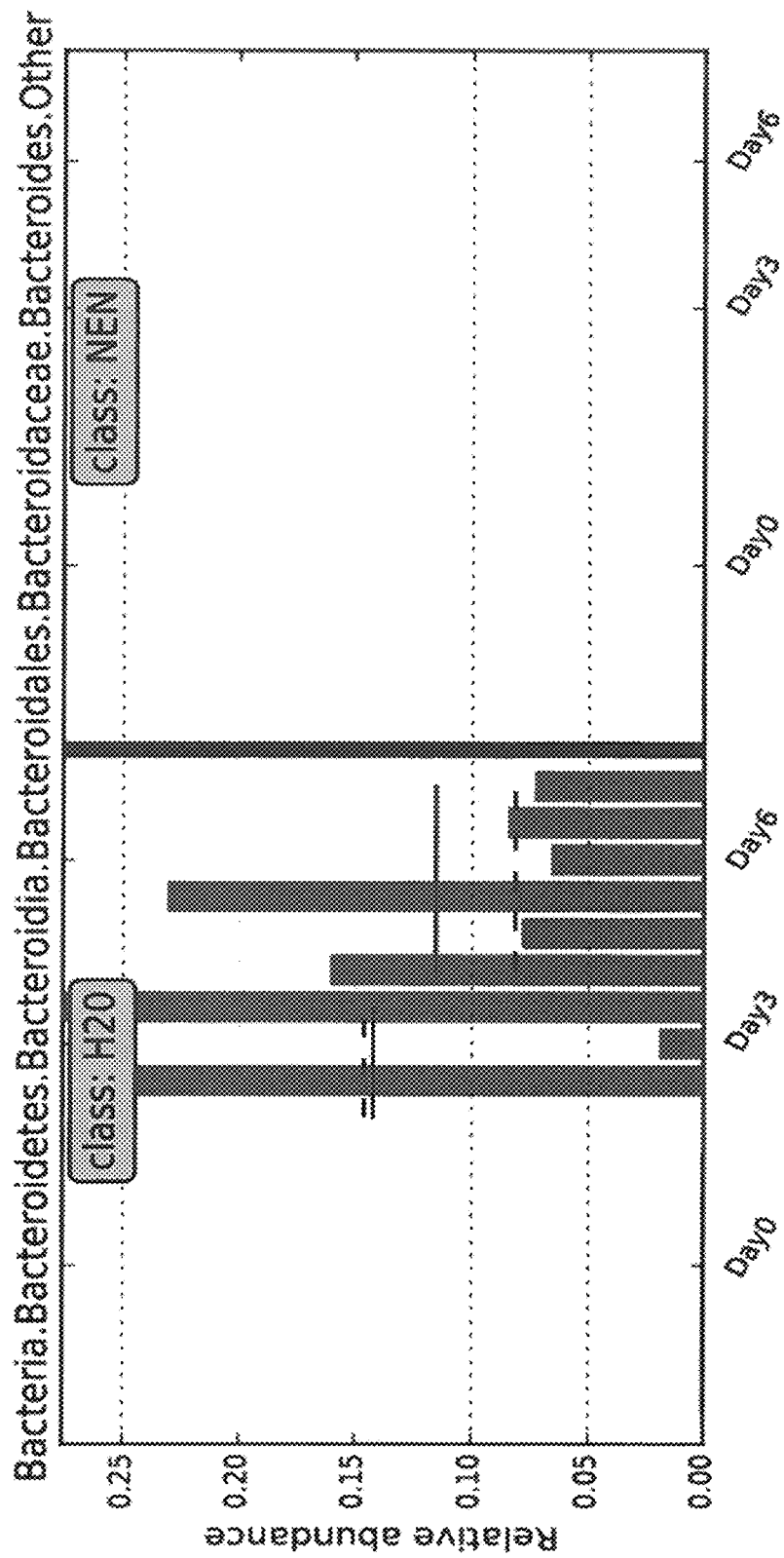
FIG. 11. Effect of treatment on the relative abundance of the genus *Bacteroides*. Bars represent the relative abundance of *Bacteroides* in each sample. Dotted line represents mean, solid line represents median relative abundance. The alpha value for the non-parametric factorial Kruskal-Wallis (KW) sum-rank test was 0.05 and the threshold for the logarithmic LDA model score for discriminative features was set at 2.0.

Next, we evaluated the effects of NEN on the gut microbiota in C. difficile-infected mice that had been pre-treated with an antibiotic cocktail 6, 5 and 4 days prior to infection and clindamycin the day prior to infection (FIG. 4b-d). The diversity of the microbiota following NEN treatment (50 mg/kg) on days 1, 2 and 3 post infection was indistinguishable from the water control group (FIG. 4b). Further, the composition and structure of the gut microbiota on day 6 post-infection did not differ from water treatment (FIG. 4b and FIG. 9), comprising of high relative abundance of Lactobacillaceae, Bifidobacteriaceae, Clostridiales and Bacteroidales, and decreased relative abundance of Enterobacteriaceae (mainly *Escherichia coli*) (FIG. 9). Linear discriminant analysis (LDA) effect size (LEfSe) analysis (38) only identified members of the genus *Bacteroides* out of 154 phylotypes as significantly more abundant on day 6 in water control than in NEN treated mice (FIG. 11).

Having shown that NEN does not affect the structure or composition of the microbiota, we next asked whether NEN (alone or combination with vancomycin) was potentially able to help restore the gut microbiota during the resolution phase of infection. To this end, we compared the effects of NEN (50 mg/kg)+vancomycin (0.5 mg/kg), and NEN (50 mg/kg) alone, to vancomycin alone, in the recurrent C. difficile model. As expected, the diversity of the gut microbiota after vancomycin treatment alone remained low throughout the treatment cycle and was dominated by Lactobacillaceae (FIGS. 4c and 4d). Whereas the addition of NEN (50 mg/kg) to vancomycin (0.5 mg/kg) showed no benefits to the microbiota compared to vancomycin alone (FIG. 4c), treatment with NEN (50 mg/kg) alone resulted in a significant increase in diversity post-treatment and during resolution of infection (FIG. 4d), indicating that NEN may have additional benefits on the gut microbiota as a stand-alone therapy.

Discussion

The global spread of epidemic strains of C. difficile capable of causing outbreaks and life-threatening infections is a recent phenomenon that has been brought on, in part, by modern human practices. The widespread introduction of the food additive trehalose, shortly before the emergence of epidemic RT027 and RT078, has been proposed to have contributing in selecting for these strains and increasing their virulence (7). Similarly, the use and misuse of antibiotics have further accelerated the enrichment of multidrug resistant variants of C. difficile, whilst disrupting the protective microbiota that normally prevents such infections (39). As a result, C. difficile continues to increasingly become more widespread, more virulent, and more difficult to treat with traditional eradication approaches (i.e., antibiotics). The notion of targeting the virulence determinants of C. difficile has emerged as an attractive alternative strategy to treat CDI (30, 40-42), especially given the role that toxins play in all aspects of disease pathogenesis (9-11, 43). The recent clinical demonstration of disease recurrence attenuation by the injectable TcdB-targeted antibody bezlotoxumab (15) supports these approaches and has fueled efforts to identify next generation antivirulence therapeutics. In particular, more convenient oral agents (i.e., small molecules) that can be dosed at all stages of disease are highly sought after. Moreover, although targeting TcdB appears to be capable of decreasing recurrence, blocking the actions of TcdA and binary toxin, both of which contribute to disease pathogenesis in hypervirulent strains and appear to be sufficient for causing disease in strains lacking TcdB in certain cases, would be a highly desirable feature of any comprehensive would-be antivirulence strategy.

In this study, we performed a high-throughput screen of libraries containing FDA- and EMEA-approved drugs to identify small-molecules that protected cells from TcdB intoxication that could potentially be repositioned as orally-bioavailable therapeutics for treating CDI. Among the dozens of hits identified in the primary screen (FIG. 6), we noted that several were approved anti-parasitic drugs. From the most potent inhibitors of cell-rounding in this class, niclosamide was selected for further characterization based on its impeccable safety profile in humans, and known preferential distribution in the lower GI after oral dosing (26), which we anticipated would be beneficial for targeting the gut-damaging toxins of C. difficile. Niclosamide is a remarkably well-studied molecule that has been shown to have a number of other biological activities in vitro that have prompted other investigations into translation into diseases including cancer (44-48), diabetes (49) as well as other infectious diseases (22). In most cases, however, the low systemic exposure of niclosamide, which is likely a major contributor to its overall safety, has hampered its use for indications outside of the GI tract. Nevertheless, efforts have been undertaken to improve the bioavailability of niclosamide, using different salt forms, chemical modifications, and the use of nanoparticles (50-52).

Figure 4:
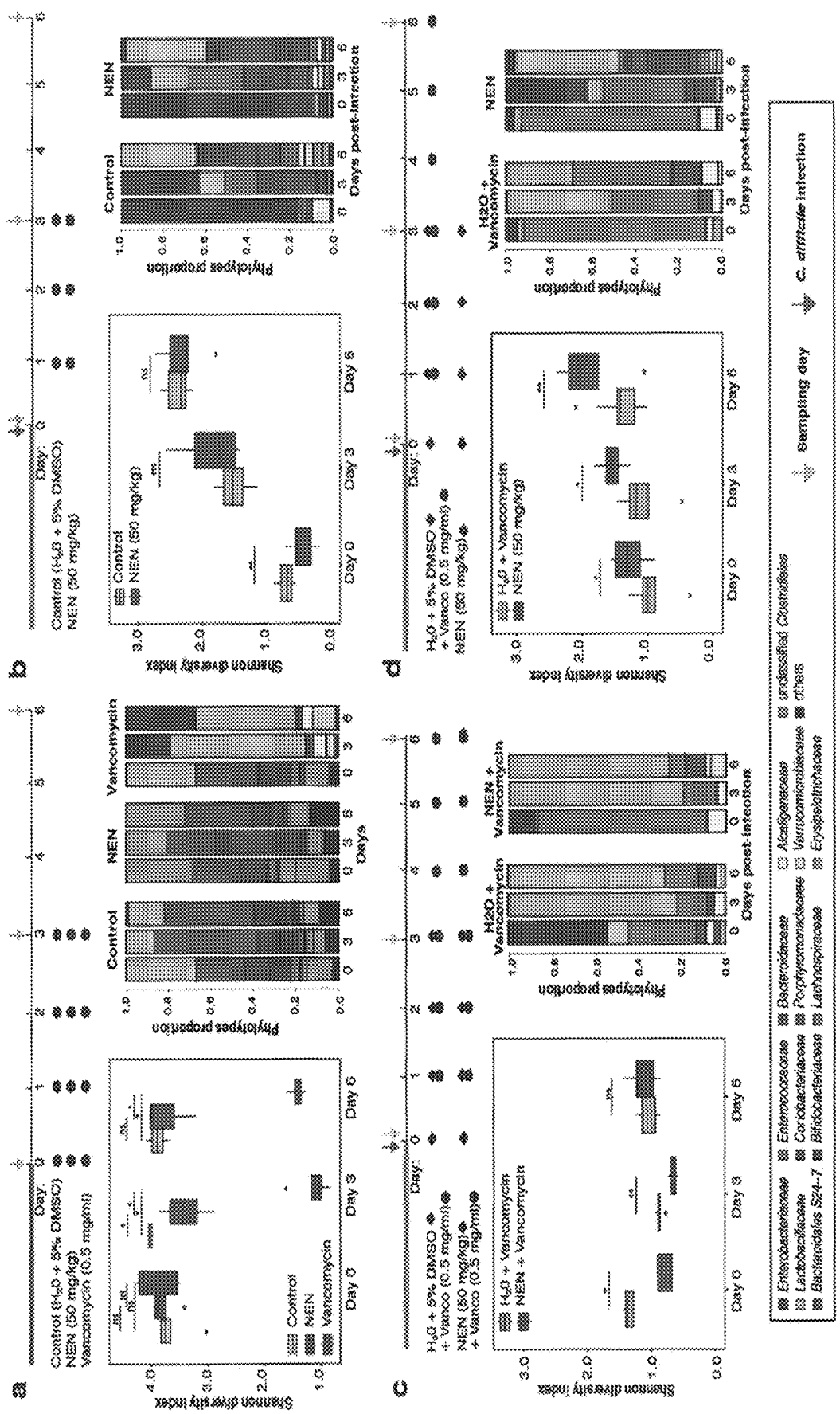
FIG. 4. Effect of treatment on the gut microbiota diversity and composition. Experimental design is shown on top panel (red line indicates antibiotic cocktail treatment six days prior to the *C. difficile* infection for three days, followed by two days of water and clindamycin (30 mg/kg) the day prior to *C. difficile* infection, green line indicates no treatment). Within-sample diversity was estimated using Shannon diversity index (ns denotes not significant, * is when p value greater than 0.01 but no greater than 0.05, ** is when p value is less than 0.01). Each treatment group is the result of two experimental cages. Each barplot indicates the mean relative abundance of bacterial families with relative abundance >1% from mice in two experimental cages. (a) control, NEN, and vancomycin treatment in the absence of *C. difficile* infection; (b) control (water with 5% DSMO) and NEN treatment (50 mg/kg); (c) water with vancomycin and NEN treatment (50 mg/kg); (d) water with vancomycin and NEN treatment (50 mg/ml) with vancomycin (0.5 mg/ml). First sampling day (day 0) is 4 hours after *C. difficile* infection.

Here, we found that niclosamide provided protection to a variety of human cells from both TcdB-induced cell-rounding, and TcdB-induced necrosis. Moreover, due to its mechanism of inhibition of TcdB (i.e., targeting host endosomal pH through a proton-shuttle mechanism), niclosamide had the added major benefit of being equally effective against TcdA and CDT—both of which also require low pH for entry into the host. These features provided the unique opportunity to test niclosamide as a stand-alone agent against epidemic strains of C. difficile that are triple-positive for TcdA, TcdB and CDT. In mouse models of CDI, we showed that NEN dose-dependently improved disease symptoms associated with both primary infection and recurrence, with full protection seen at 50 mg/kg NEN. Of note, the reported median oral lethal dose ($LD_{50}$) for NEN in rats is 10,000 mg/kg body weight (27), further emphasizing the large therapeutic index for NEN in treating CDI. Finally, an important and significant finding in this study was that NEN had no major deleterious effects on the structure and composition of the microbiota (FIG. 4). Increased diversity of the gut microbiota was observed after NEN treatment, a feature that was thought to be unique to fecal microbiota transplantation and key to its success. Recovery of a diverse microbiota might in part contribute to it curative properties.

REFERENCES

1. C. M. Theriot, A. A. Bowman, V. B. Young, Antibiotic-Induced Alterations of the Gut Microbiota Alter Secondary Bile Acid Production and Allow for *Clostridium difficile* Spore Germination and Outgrowth in the Large Intestine. mSphere 1, (2016).
2. L. C. McDonald et al., An epidemic, toxin gene-variant strain of *Clostridium difficile*. N Engl J Med 353, 2433-2441 (2005).
3. A. Goorhuis et al., Emergence of *Clostridium difficile* infection due to a new hypervirulent strain, polymerase chain reaction ribotype 078. Clin Infect Dis 47, 1162-1170 (2008).
4. D. N. Gerding, S. Johnson, M. Rupnik, K. Aktories, *Clostridium difficile* binary toxin CDT: mechanism, epidemiology, and potential clinical importance. Gut Microbes 5, 15-27 (2014).
5. M. He et al., Emergence and global spread of epidemic healthcare-associated *Clostridium difficile*. Nature genetics 45, 109-113 (2013).
6. M. Warny et al., Toxin production by an emerging strain of *Clostridium difficile* associated with outbreaks of severe disease in North America and Europe. Lancet 366, 1079-1084 (2005).
7. J. Collins et al., Dietary trehalose enhances virulence of epidemic *Clostridium difficile*. Nature, (2018).
8. J. M. Lanis, S. Barua, J. D. Ballard, Variations in TcdB activity and the hypervirulence of emerging strains of *Clostridium difficile*. PLoS Pathog 6, e1001061 (2010).
9. D. Lyras et al., Toxin B is essential for virulence of *Clostridium difficile*. Nature 458, 1176-1179 (2009).
10. S. A. Kuehne et al., The role of toxin A and toxin B in *Clostridium difficile* infection. Nature 467, 711-713 (2010).
11. S. A. Kuehne et al., Importance of toxin A, toxin B, and CDT in virulence of an epidemic *Clostridium difficile* strain. J Infect Dis 209, 83-86 (2014).
12. T. M. Louie et al., paper presented at the ium *difficile*-associated diarrhea (CDAD), poster K-425a, p. 212. Abstr. 47th Intersci. Conf. Antimicrob. Agents Chemother. American Society for Microbiology, Washington, D C, 2007.
13. Z. Zhang et al., Toxin-mediated paracellular transport of antitoxin antibodies facilitates protection against *Clostridium difficile* infection. Infect Immun 83, 405-416 (2015).
14. W. D. Kufel, A. S. Devanathan, A. H. Marx, D. J. Weber, L. M. Daniels, Bezlotoxumab: A Novel Agent for the Prevention of Recurrent *Clostridium difficile* Infection. Pharmacotherapy 37, 1298-1308 (2017).
15. M. H. Wilcox et al., Bezlotoxumab for Prevention of Recurrent *Clostridium difficile* Infection. N Engl J Med 376, 305-317 (2017).
16. P. Spigaglia et al., *Clostridium difficile* causing pediatric infections: New findings from a hospital-based study in Italy. Anaerobe, (2017).
17. P. Spigaglia, F. Barbanti, M. Morandi, M. L. Moro, P. Mastrantonio, Diagnostic testing for *Clostridium difficile* in Italian microbiological laboratories. Anaerobe 37, 29-33 (2016).
18. G. O. Androga et al., Infection with Toxin A-Negative, Toxin B-Negative, Binary ToxinPositive *Clostridium difficile* in a Young Patient with Ulcerative Colitis. J Clin Microbiol 53, 3702-3704 (2015).
19. S. Grandesso et al., *Clostridium difficile* ribotype 033 colitis in a patient following broadspectrum antibiotic treatment for KPC producing *Klebsiella pneumoniae* infection, Italy. New Microbiol 39, 235-236 (2016).
20. C. Eckert et al., Prevalence and pathogenicity of binary toxin-positive *Clostridium difficile* strains that do not produce toxins A and B. New Microbes New Infect 3, 12-17 (2015).
21. C. Z. Chen et al., High-throughput *Giardia lamblia* viability assay using bioluminescent ATP content measurements. Antimicrob Agents Chemother 55, 667-675 (2011).
22. M. Xu et al., Identification of small-molecule inhibitors of Zika virus infection and induced neural cell death via a drug repurposing screen. Nat Med 22, 1101-1107 (2016).
23. L. M. Johansen et al., A screen of approved drugs and molecular probes identifies therapeutics with anti-Ebola virus activity. Science translational medicine 7, 290ra289 (2015).
24. S. He et al., Repurposing of the antihistamine chlorcyclizine and related compounds for treatment of hepatitis C virus infection. Science translational medicine 7, 282ra249 (2015).
25. R. D. Pearson, E. L. Hewlett, Niclosamide therapy for tapeworm infections. Ann Intern Med 02, 550-551 (1985).
26. P. Andrews, J. Thyssen, D. Lorke, The biology and toxicology of molluscicides, Bayluscide. Pharmacol Ther 19, 245-295 (1982).
27. G. Hecht, C. Gloxhuber, [Studies on the tolerance of 5,2'-dichloro-4'-nitrosalicylanilide ethanolamine salt]. Z Tropenmed Parasitol 13, 1-8 (1962).
28. S. T. Donta, N. Sullivan, T. D. Wilkins, Differential effects of *Clostridium difficile* toxins on tissue-cultured cells. J Clin Microbiol 15, 1157-1158 (1982).
29. M. Qa'Dan et al., *Clostridium difficile* toxin B activates dual caspase-dependent and caspase-independent apoptosis in intoxicated cells. Cell Microbiol 4, 425-434 (2002).
30. J. Tam et al., Small molecule inhibitors of *Clostridium difficile* toxin B-induced cellular damage. Chem Biol 22, 175-185 (2015).
31. A. Eniu, J. Torode, N. Magrini, G. Bricalli, E. M. L. S. C. M. Union for International Cancer Control, Back to the 'essence' of medical treatment in oncology: the 2015 WHO Model List of Essential Medicines. ESMO Open 1, e000030 (2016).
32. M. A. Farrow et al., *Clostridium difficile* toxin B-induced necrosis is mediated by the host epithelial cell NADPH oxidase complex. Proc Natl Acad Sci USA 110, 18674-18679 (2013).
33. Z. Zhang et al., Translocation domain mutations affecting cellular toxicity identify the *Clostridium difficile* toxin B pore. Proc Natl Acad Sci USA 111, 3721-3726 (2014).

34. M. Gooyit, K. D. Janda, Reprofiled anthelmintics abate hypervirulent stationary-phase *Clostridium difficile*. Scientific reports 6, 33642 (2016).
35. K. Pauk et al., New derivatives of salicylamides: Preparation and antimicrobial activity against various bacterial species. Bioorg Med Chem 21, 6574-6581 (2013).
36. C. J. Hastey et al., Comparison of *Clostridium difficile* minimum inhibitory concentrations obtained using agar dilution vs broth microdilution methods. Anaerobe 44, 73-77 (2017).
37. G. W. Tannock et al., A new macrocyclic antibiotic, fidaxomicin (OPT-80), causes less alteration to the bowel microbiota of *Clostridium difficile*-infected patients than does vancomycin. Microbiology 156, 3354-3359 (2010).
38. N. Segata et al., Metagenomic biomarker discovery and explanation. Genome Biol 12, R60 (2011).
39. C. Slimings, T. V. Riley, Antibiotics and hospital-acquired *Clostridium difficile* infection: update of systematic review and meta-analysis. J Antimicrob Chemother 69, 881-891 (2014).
40. G. L. Beilhartz, J. Tam, R. A. Melnyk, Small Molecules Take A Big Step Against *Clostridium difficile*. Trends Microbiol 23, 746-748 (2015).
41. G. L. Beilhartz, J. Tam, Z. Zhang, R. A. Melnyk, Comment on "A small-molecule antivirulence agent for treating *Clostridium difficile* infection". Science translational medicine 8, 370tc372 (2016).
42. K. O. Bender et al., A small-molecule antivirulence agent for treating *Clostridium difficile* infection. Science translational medicine 7, 306ra148 (2015).
43. G. P. Carter et al., Defining the Roles of TcdA and TcdB in Localized Gastrointestinal Disease, Systemic Organ Damage, and the Host Response during *Clostridium difficile* Infections. MBio 6, e00551 (2015).
44. M. A. Suliman et al., Niclosamide inhibits colon cancer progression through downregulation of the Notch pathway and upregulation of the tumor suppressor miR-200 family. Int J Mol Med 38, 776-784 (2016).
45. L. Chen, L. Wang, H. Shen, H. Lin, D. Li, Anthelminthic drug niclosamide sensitizes the responsiveness of cervical cancer cells to paclitaxel via oxidative stress-mediated mTOR inhibition. Biochem Biophys Res Commun 484, 416-421 (2017).
46. M. Xiang et al., Niclosamide enhances the antitumor effects of radiation by inhibiting the hypoxia-inducible factor-1alpha/vascular endothelial growth factor signaling pathway in human lung cancer cells. Oncol Lett 14, 1933-1938 (2017).
47. X. Yu et al., Niclosamide Exhibits Potent Anticancer Activity and Synergizes with Sorafenib in Human Renal Cell Cancer Cells. Cell Physiol Biochem 47, 957-971 (2018).
48. Y. Zuo et al., Niclosamide enhances the cytotoxic effect of cisplatin in cisplatin-resistant human lung cancer cells via suppression of lung resistance-related protein and c-myc. Mol Med Rep 17, 3497-3502 (2018).
49. H. Tao, Y. Zhang, X. Zeng, G. I. Shulman, S. Jin, Niclosamide ethanolamine-induced mild mitochondrial uncoupling improves diabetic symptoms in mice. Nat Med 20, 1263-1269 (2014).
50. C. K. Lin et al., Preclinical evaluation of a nanoformulated antihelminthic, niclosamide, in ovarian cancer. Oncotarget 7, 8993-9006 (2016).
51. J. Bhattacharyya et al., Niclosamide-conjugated polypeptide nanoparticles inhibit Wnt signaling and colon cancer growth. Nanoscale 9, 12709-12717 (2017).
52. S. Naqvi, S. Mohiyuddin, P. Gopinath, Niclosamide loaded biodegradable chitosan nanocargoes: an in vitro study for potential application in cancer therapy. R Soc Open Sci 4, 170611 (2017).
53. G. Yang et al., Expression of recombinant *Clostridium difficile* toxin A and B in *Bacillus megaterium*. BMC Microbiol 8, 192 (2008).
54. S. Bagrodia, S. J. Taylor, C. L. Creasy, J. Chernoff, R. A. Cerione, Identification of a mouse p21Cdc42/Rac activated kinase. J Biol Chem 270, 22731-22737 (1995).

55. L. H. Slater et al., Identification of novel host-targeted compounds that protect from anthrax lethal toxin-induced cell death. ACS Chem Biol 8, 812-822 (2013).

56. F. H. Niesen, H. Berglund, M. Vedadi, The use of differential scanning fluorimetry to detect ligand interactions that promote protein stability. Nat Protoc 2, 2212-2221 (2007).

57. P. Orth et al., Mechanism of action and epitopes of *Clostridium difficile* toxin B-neutralizing antibody bezlotoxumab revealed by X-ray crystallography. J Biol Chem 289, 18008-18021 (2014).

58. D. W. Fadrosh et al., An improved dual-indexing approach for multiplexed 16S rRNA gene sequencing on the Illumina MiSeq platform. Microbiome 2, 6 (2014). 59. vol. 2017.

60. R. Schmieder, Y. W. Lim, F. Rohwer, R. Edwards, TagCleaner: Identification and removal of tag sequences from genomic and metagenomic datasets. BMC Bioinformatics 11, 341 (2010).

61. B. J. Callahan et al., DADA2: High-resolution sample inference from Illumina amplicon data. Nature methods 13, 581-583 (2016).

62. R. C. Edgar, H. Flyvbjerg, Error filtering, pair assembly and error correction for nextgeneration sequencing reads. Bioinformatics 31, 3476-3482 (2015).

63. D. McDonald et al., An improved Greengenes taxonomy with explicit ranks for ecological and evolutionary analyses of bacteria and archaea. Isme J 6, 610-618 (2012).

64. S. J. Bent, L. J. Forney, The tragedy of the uncommon: understanding limitations in the analysis of microbial diversity. ISME J 2, 689-695 (2008).

65. P. J. McMurdie, S. Holmes, phyloseq: an R package for reproducible interactive analysis and graphics of microbiome census data. PLoS One 8, e61217 (2013).

66. W. H. Kruskal, W. A. Wallis, Use of ranks in one-criterion variance analysis. J. Am Stat Assoc 47, 583-621 (1952).

67. R. A. Fisher, The use of multiple measurements in taxonomic problems. Ann Eugenics 7, (1936).

The above disclosure generally describes the present invention. Although specific terms have been employed herein, such terms are intended in a descriptive sense and not for purposes of limitation.

All publications, patents and patent applications cited above are herein incorporated by reference in their entirety to the same extent as if each individual publication, patent or patent application was specifically and individually indicated to be incorporated by reference in its entirety.

Although preferred embodiments of the invention have been described herein in detail, it will be understood by those skilled in the art that variations may be made thereto without departing from the spirit of the invention or the scope of the appended claims.

The invention claimed is:

1. A method of reducing virulence of an enteric toxigenic pathogen, the method comprising administering a salicylanilide to a host infected with or at risk of infection with the pathogen, wherein the salicylanilide is used in an amount that affects host cells without substantially killing the pathogen and/or disrupting the gut microbiota.

2. The method of claim 1, wherein the host does not currently have an active or clinically relevant infection caused by the pathogen.

3. The method of claim 2, wherein the pathogen is bacteria.

4. The method of claim 3, wherein the bacteria is *Clostridium, Vibrio cholerae,* or *E. coli.*

5. The method of claim 4, wherein the *Clostridium* is *C. difficile.*

6. The method of claim 5, wherein the *C. difficile* is selected from ribotype 017, 027, 033, and 078.

7. The method of claim 5, wherein the *Clostridium* expresses TcdA, and/or TcdB, and/or CDT.

8. The method of claim 7, wherein the method reduces virulent toxin entry into host cells.

9. The method of claim 1, wherein the salicylanilide is selected from the group consisting of bromochlorosalicylanilide, tetrachlorosalicylanilide, closantel, rafoxanide, oxyclozanide, resorantel, clioxanide, dibromosalan, tribromosalan, brotianide, niclosamide, salts thereof, esters thereof, derivatives thereof, and analogs thereof.

10. The method of claim 9, wherein the salicylanilide is niclosamide ethanolamine (NEN).

11. The method of claim 1, wherein the salicylanilide is not niclosamide.

12. The method of claim 1, wherein
a) the salicylanilide maintains gut microbiota diversity, composition, and/or structure;
b) the method does not cause antibiotic-induced dysbiosis of the GI microbiota;
c) the method at least partially restores the gut microbiota during the resolution phase of infection;
d) the method at least partially inhibits host damage induced by toxins without substantially altering the gut microbiota;
e) the salicylanilide acts on host cells through inhibition of the pore-formation process;
f) the salicylanilide increases the pH of host cell endosomal compartments;
g) the salicylanilide inhibits the pathogenesis of enterogenic toxins by targeting a host process required for entry into colonocytes by each toxin;
h) the salicylanilide protects the host from pathogen-related weight loss, death, and/or diarrhea; and/or
i) the method reduces primary infection and/or recurrence of infection.

13. The method of claim 12, wherein the salicylanilide inhibits the pathogenesis of enterogenic toxins by targeting a host process required for entry into colonocytes by each toxin and the toxins are selected from TcdA, and/or TcdB, and/or CDT.

14. The method of claim 13, wherein the toxins are TcdA, TcdB, and CDT.

15. The method of claim 1, wherein the salicylanilide is used as a stand-alone therapy.

16. The method of claim 1, wherein the method is used as a first line therapy.

17. The method of claim 1, wherein the method is used as a second line therapy once conventional antibiotics fail.

18. The method of claim 1, wherein the method is for reducing recurrence and is for use after a conventional treatment.

19. The method of claim 1, wherein the salicylanilide is used in combination with an antibiotic.

* * * * *

UNITED STATES PATENT AND TRADEMARK OFFICE
CERTIFICATE OF CORRECTION

PATENT NO. : 11,166,926 B2  
APPLICATION NO. : 16/535658  
DATED : November 9, 2021  
INVENTOR(S) : Melnyk et al.

Page 1 of 1

It is certified that error appears in the above-identified patent and that said Letters Patent is hereby corrected as shown below:

In the Specification

Column 4, Line 17: Please correct "0.5 μM" to read -- 0.5 pM --

Column 9, Line 40: Please insert a page break between "modality." and "In"

Column 14, Line 30: Please correct "100 μM" to read -- 100 pM --

Column 17, Line 37: Please correct "1 μM" to read -- 1 pM --

Column 18, Line 2: Please correct "0.8 μM (FIG. 10." to read -- 0.8 pM (FIG. *1f*). --

Signed and Sealed this  
Twenty-ninth Day of March, 2022

Drew Hirshfeld  
*Performing the Functions and Duties of the*  
*Under Secretary of Commerce for Intellectual Property and*  
*Director of the United States Patent and Trademark Office*